United States Patent [19]

Hercend et al.

[11] Patent Number: 5,976,877
[45] Date of Patent: *Nov. 2, 1999

[54] PROTEINS PRODUCED BY HUMAN LYMPHOCYTES DNA SEQUENCE ENCODING THESE PROTEINS AND THEIR PHARMACEUTICAL AND BIOLOGICAL USES

[75] Inventors: Thierry Hercend, Charenton; Frédéric Triebel, Versailles, both of France

[73] Assignees: Institut National De La Sante Et De La Recherche Medicale (Inserm), Paris, France; Institut Gustave Roussy, Villejuif, France; Applied Research Systems ARS Holding N.V., Curacao, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/394,442

[22] Filed: Feb. 24, 1995

Related U.S. Application Data

[63] Continuation of application No. 07/922,466, Jul. 10, 1992, abandoned, which is a continuation-in-part of application No. 07/854,644, Sep. 8, 1992, abandoned, which is a continuation of application No. PCT/FR91/00009, Jan. 8, 1991.

[30] Foreign Application Priority Data

Jan. 8, 1990 [FR] France ................................ 90 00 126

[51] Int. Cl.$^6$ ........................ A61K 39/395; C07K 16/28; C12N 5/12; C12N 5/20
[52] U.S. Cl. ...................... 435/343.2; 435/331; 435/334; 435/343.2; 435/326; 530/387.1; 530/387.9; 530/388.75; 530/391.1; 530/391.3; 530/391.7; 530/809; 530/866; 530/388.22; 424/133.1; 424/135.1; 424/139.1; 424/144.1; 424/154.1; 424/178.1; 424/183.1; 424/1.49
[58] Field of Search ............................ 424/133.1, 135.1, 424/139.1, 144.1, 154.1, 178.1, 183.1, 1.49; 435/240.27, 331, 334, 343.2, 326; 530/387.1, 387.9, 388.75, 391.1, 391.3, 391.7, 809, 866, 388.22

[56] References Cited

U.S. PATENT DOCUMENTS 5,109,123  4/1992  Reinherz et al. ..................... 536/23.72

FOREIGN PATENT DOCUMENTS 0 320 806   6/1989   European Pat. Off. .
0 329 363   8/1989   European Pat. Off. .

OTHER PUBLICATIONS

Amzel, L.M. and Poljak, R.J., "Three–Dimensional Structure of Immunoglobulins", *Ann. Rev. Biochem. 48:*961–997 (1979).

Aviv, H. et al., "Purification of Biologically Active Globin Messenger RNA by Chromatography on Oligothymidylic acid–Cellulose", *Proc. Natl. Acad. Sci. USA* 69(6): 1408–1412 (Jun. 1972).
Bowie et al., "Deciphering the Message in Protein Sequences: Tolerance to Amino Acid Substitutions", *Science* 247:1306–1310 (Mar. 1990).
Byrn, R.A. et al., "Biological properties of a CD4 immunoadhesin", *Nature* 344:667–670 (Apr. 12, 1990).
Chang, N.T. et al., "A cDNA clone encoding a product of activated human T lymphocytes", *Chem. Abstracts 102:*181, Abstract 216258n (1985).
Dariavach P. et al., "Human immunoglobulin $C_\lambda 6$ encodes the Kern $^+$Oz$^-$ λ chain and $C_\lambda 4$ and $C_\lambda 5$ are pseudogenes", *Proc. Natl. Acad. Sci. USA* 84:9074–9078 (Dec. 1987).
Davis, M. M. et al., "Cell–type–specific cDNA probes and the murine I region: The localization and orientation of $A_\alpha^d$" *Proc. Natl. Acad. Sci. USA* 81:81:2194–2198 (Apr. 1984).
Dayhoff, M.O. et al., "Establishing Homologies in Protein Sequences", *Methods Enzymol.* 91:524–45 (1983).
Feinberg, A.P. et al., "A Technique for Radiolabeling DNA Restriction Endonuclease Fragments to High Specific Activity", *Anal. Biochem.* 132:6–13 (1983).
Goding, "Production of Monoclonal Antibodies", Chapter 3 in: Goding, Academic Press, *Monoclonal Antibodies: Principles and Practices:*59–103 (1986).
Gubler, U. and Hoffman,B.J., "A simple and very efficient method for generating cDNA libraries", *Gene.* 25:263–269 (1983).
Hart, C.E. et al., "Human Chromosome 12 is Required for Elevated HIV–1 Expression in Human–Hamster Hybrid Cells", *Science* 246:488–491 (Oct. 27, 1989).
Huynh, T.V. et al., "Constructing and Screening cDNA Libraries in λgt10 and λgt11" D. Glover (ed), IRL Press. Oxford, UK, *DNA cloning: A practical approach:*49–78.
Jongstra, J. et al., "The Isolation and Sequence of a Novel Gene from a Human Functional T Cell Line", *J. Exp. Med.* 165:601–614 (Mar. 1987).
Kirszbaum, L. et al., "The α–Chain of Murine CD8 Lacks an Invariant Ig–Like Disulfide Bond but Contains a Unique Intrachain Loop Instead", *J. Immunol.* 142(11):3931–3936 (Jun. 1, 1989).
Lesk, A.M. and Chothia, C., "Evolution of Proteins Formed by β–Sheets", *J. Mol. Biol.* 160:325–342 (1982).
Luckow, V.A. et al., "Trends in the Development of Baculovirus Expression Vectors", *Bio/Technology* 6:47–55 (Jan. 1988).
Maddon, P.J. et al., "Structure and Expression of the Human and Mouse T4 Genes", *Proc. Natl. Acad. Sci. USA* 84:9155–9159 (1987).

(List continued on next page.)

*Primary Examiner*—Ronald B. Schwadron
*Attorney, Agent, or Firm*—Browdy & Neimark

[57] ABSTRACT

Disclosed herein are monoclonal antibodies which specifically bind a protein comprising the peptide sequence represented by the sequence SEQ ID No. 1 or an immunogenic sequence of such a protein and derivatives and fragments thereof, as well as hybridomas useful for preparing them and pharmaceutical compositions in which they can be used.

6 Claims, 13 Drawing Sheets

OTHER PUBLICATIONS

Marlin, S.D. et al., "A soluble form of intercellular adhesion molecule–1 inhibits rhinovirus infection", *Nature 344:*70–72 (Mar. 1, 1990).

Mechler, B. et al., "Membrane–bound Ribosomes of Myeloma Cells IV. mRNA Complexity of Free and Membrane–bound Polysomes", *J. Cell. Biol. 88:*29–36 (Jan. 1981).

Moingeon, P. et al., "A unique T–cell receptor complex expressed on human fetal lymphocytes displaying natural–killer–like activity", *Nature 323:*638–640 (Oct. 16, 1986).

Nowill, A. et al., "Natural Killer Clones Derived From Fetal (25wk) Blood", *J. Exp. Med. 163:*1601–1606 (Jun. 1986).

Ratner, L. et al., "Complete nucleotide sequence of the AIDS virus, HTLV–III", *Nature 313:*277–284 (Jan. 24, 1985).

Ruoslahti, E. et al., "Arg–Gly–Asp: A Versatile Cell Recognition Signal", *Cell 44:*517–518 (Feb. 28, 1986).

Ryu, S.–E. et al., "Crystal structure of an HIV–binding recombinant fragment of human CD4", *Nature 348:*419–426 (Nov. 29, 1990).

Sanger, F.et al., "DNA sequencing with chain–terminating inhibitors",*Proc. Natl. Acad. Sci. USA 74(12)*:5463–7 (Dec. 1977).

Santoni, M.J. et al., "Differential exon usage involving an unusual splicing mechanism generates at least eight types of NCAM cDNA in mouse brain", *EMBO J. 8(2)*:385–392 (1989).

Seed, B., "An LFA–3–cDNA encodes a phospholipid linked membrane protein homologous to its receptor CD2", *Nature 329:*840–842 (Oct. 29, 1987).

Staunton, D.E and Thorley–Lawson, D.A., "Molecular cloning of the lymphocyte activation marker Blast–1", *EMBO J. 6(12)*:3695–3701 (1987).

Staunton, D.E. et al., "The Arrangement of the Immunoglobulin–like Domains of ICAM–1 and the Binding Sites for LFA–1", *Cell 61:*243–254 (Apr. 20, 1990).

Triebel, F. et al., "Cloned human CD3⁻ lymphocytes with natural killer– like activity do not express nor rearrange T cell receptor gamma genes",*Eur. J. Immunol. 17:*1209–1212 (1987).

Wang, J. et al., "Atomic structure of a fragment of human CD4 containing two immunoglobulin–like domains", *Nature 348:*411–418 (Nov. 29, 1990).

Wegner, C.D. et al., "Intercellular Adhesion Molecule–1 (ICAM–1) in the Pathogenesis of Asthma", *Science 247:*456–459 (Jan. 26, 1990).

Williams, A.F., "A year in the life of the immunoglobulin superfamily", *Immunol. Today 8(10)*:298–303 (1987).

Williams, A.F. et al., "the Immunoglobulin Superfamily–Domains for Cell Surface Recognition",*Ann. Rev. Immunol. 6:*381–405 (1988).

Yourno, J. et al., "Nucleotide Sequence Analysis of the env Gene of a New Zairian Isolate of HIV–1", *AIDS Res. Hum. Retroviruses 4(3)*:165–173 (1988).

Ythier, A. et al., "Generation of Monoclonal Antibodies Blocking Cytotoxic Reactions by Human NK Clones: Further Characterization of a 40/80–kDa Target Cell Receptor", *Cell Immunol. 99:*150–159 (1986).

Borrebaeck et al., Imm. Today, 14: 477–479, 1993.

Foon, Canc. Res., 49: 1621–39, 1989.

Harris et al., TIBTECH, vol. 11, pp. 42–44, 1993.

Waldmann, Science, vol. 262, 1657–1662, 1991.

Triebel et al., J. Exp. Med., vol. 171, pp. 1393–1405, 1990.

Goding, Chapters 4 and 8, "Monoclonal Antibodies: Principles and Practices", Academic Press, 1986.

FIG. 5

```
         ...D....    ..E....              ...F...       ....G....         ...A...
  91  RVQLDERGRQRGDFSLWLRPARRADAGEYRAAVHLRDRALSCRLRLRL-GQASMTASPPG
 276  GPDLLVTG-DNGDFTLRLEDVSQAQAGTYTCHIHLQEQQLNATVTLAIITVTPKSFGSPG
        .*  .  ***.*.*       .*.** *.   .**... *.  . * .    .. .  .**

..      ...B...    ...C...       ....D....       ...E....       ..
 150  SLRASDWVILNCSFSRPDRPASVHWFRNRGQGRVPVRESPHHHLAESFLFLPQVSPMDSG
 335  SL-----GKLLCEVTPVSGQERFVW--------SSLDTPSQRSFSGPWL-EAQEAQLLSQ
       ,**      * *   .         *           ..  .... .. .*  *  . . *

..F.....    ....G...
 210  PWGCILTYRDGFNVSIM-YNLTVLGLEP..
 381  PWQCQL-YQGERLLGAAVY-FTELSS-PGA
      ** * * *..   ..    * .* *    *
```

FIG. 6

```
              L    ↓         ..A.,      ...B....
LAG-3 MWEAQFLGLLFLQPLWVAPVKPLQPGAEVPVVWAQEGAPAQLPCSPTIPLQDLSLLRR-A
CD4   MCRGFSFRHL-LPLLLLQLSKLLVVTQGKTVVLGKEGGSAELPCESTS--------RRSA
      * . . ** * . ↑* *       ** ..**..*.*** .*           ** *

..C...   ↓                            ....C'... ..C"..  ..
   32 GVTWQHQPDSGPPAAAPGHPLAPGPHPAAPSSWGPRPRRYTVLSVGPGGLRSGRLPLQPR
   25 SFAWKSSDQ---------------------------KTILGYKNKLLIKGSLELYSR
      . .*.  .                             *.*.    * * * * .*
                                                              ↑
      ..D....   ...E...     ...F...     .....G....  ↓...A...
   92 VQLDERGRQRGDFSLWLRPARRADAGEYRAAVHLRDRALSCR-LRLRLGQASMTASPPGS
   55 FDSRKNAWERGSFPLIINKLRMEDSQTYVCELENKKEEVELWVFR-------VTFNPGTR
      •    •..** *.*  •    * *. *   *..  .  .  .*       .*  .*
                                                              ↑
      .   ....B..      ...C...     ....D....    ...E....    •
  151 LRASDWVILNCSFSRPDRPASVHWFRNRGQGRVPVRESPHHHLAESFLFLPQVSPM--DS
  108 LLQGQSLTLILD-SNPKVSDPPIECKHKSSNIV---------KDSKAFSTH-SLRIQDS
      *  .. . *    * *  .       ... *         .* *  . *    **

....F....       ...G...↓    ...A...     ...B....   ...
  209 GPWGCILTYRDGFNVSIMYNLTVLGLEPP-TPLTVYAGAGSRVGLPCRLPAGVGTRSFLT
  156 GIWNCTVTLNQKKHSFDM-KLSVLGFASTSITAYKSEGESAEFSFPLNL--GEES-LQGE
      * * *.*  . .   *    *.****.. .    *  ..  *   *  *   .
                              ↑
      .C..                                ....D..    .....E....    ....
  268 AKWTPPG-----------------------GGPDLLVTGDNGDFTLRLEDVSQAQAGTYT
  212 LRWKAEKAPSSQSWITFSLKNQKVSVQKSTSNPKFQLS-ETLPLTLQIPQVSLQFAGSGN
      .* .                            • *  ...   .***.. .** **.

F.....     ....G.... ↓  ....A..   ...B....     .....C...
  305 CHIHLQEQQLNATVTLAIITVTPKSFGSPGSLGKLLCEV-TPVSGQERFVWSSSLDTRSQR
  371 LTLTLDRGILYQEVNLVVMKVTQ-----PDS-NTLTCEVMGPTSPKMRLILKQENQEARV
      • *.   *  *  * *  .. **     *.* * ***  * * . *..       • ..
                              ↑
      ....E.....      ...F....    ...G...     ↓
  364 SFSGPWLEAQEAQLLSQPWQCQLYQGERLLGAAVYFTELSSPGAQRSGRAPGALPAGHLL
  325 SRQEKVIQVQAPE--AGVWQCLLSEGEEVKMDSKIQV-LSKGLNQ------------TMF
      *    .. *  ..   *** * .**  .    . ↑ **     *              .

TM               ↓  .
  424 LFLTLGVL-SLLLLVTGAFGFHLWRRQWRPRRFSALEQGIHPRRLRAR.............
  370 LAVVLGSAFSFLVF-TGLCILFCVRCRHQQRQAARMSQIK--RLLSEKKTCQCSHRMQKS
      * . **  *.*.. **     •   *    *..  *    ** . *    * *   . ↑
                                     ↑
        ....
  427 HNLI
```

Immunoprecipitation of membrane proteins of PHA-blasts well No. 1 : preimmune hetero-antiserum well No. 2 : hetero-antiserum well No. 3 : non-immunoprecipitant Mab well No. 4 : anti-CD2 Mab "Western blot" detection of LAG-3S using a hetero-antiserum in the baculovirus system:

well No. 1 : LAG-3S supernatant well No. 2 : LAG-3S supernatant well No. 3 : AcNPV supernatant well No. 4 : LAG-3S supernatant revealed by a preimmune hetero-antiserum;

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 1871 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 231..1724

(xi) SEQUENCE DESCRIPTION: SEQ ID NO:1:

```
TCAGGCTGCC TGATCTGCCC AGCTTTCCAG CTTTCCTCTG GATTCCGGCC TCTGGTCATC        60

CCTCCCCACC CTCTCTCCAA GGCCCTCTCC TGGTCTCCCT TCTTCTAGAA CCCCTTCCTC       120

CACCTCCCTC TCTGCAGAAC TTCTCCTTTA CCCCCCACCC CCCACCACTG CCCCCTTTCC       180

TTTTCTGACC TCCTTTTGGA GGGCTCAGCG CTGCCCAGAC CATAGGAGAG ATG TGG          236
                                                      Met Trp
                                                      -28

GAG GCT CAG TTC CTG GGC TTG CTG TTT CTG CAG CCG CTT TGG GTG GCT         284
Glu Ala Gln Phe Leu Gly Leu Leu Phe Leu Gln Pro Leu Trp Val Ala
    -25                 -20                 -15

CCA GTG AAG CCT CTC CAG CCA GGG GCT GAG GTC CCG GTG GTG TGG GCC         332
Pro Val Lys Pro Leu Gln Pro Gly Ala Glu Val Pro Val Val Trp Ala
-10                  -5                  1               5
```

| | | | | | | | | | | | | | | | |
|---|---|---|---|---|---|---|---|---|---|---|---|---|---|---|---|
| CAG | GAG | GGG | GCT | CCT | GCC | CAG | CTC | CCC | TGC | AGC | CCC | ACA | ATC | CCC | CTC | 380 |
| Gln | Glu | Gly | Ala | Pro | Ala | Gln | Leu | Pro | Cys | Ser | Pro | Thr | Ile | Pro | Leu |
| | | | 10 | | | | 15 | | | | 20 | | | | |

```
CAG GAG GGG GCT CCT GCC CAG CTC CCC TGC AGC CCC ACA ATC CCC CTC        380
Gln Glu Gly Ala Pro Ala Gln Leu Pro Cys Ser Pro Thr Ile Pro Leu
            10                  15                  20

CAG GAT CTC AGC CTT CTG CGA AGA GCA GGG GTC ACT TGG CAG CAT CAG        428
Gln Asp Leu Ser Leu Leu Arg Arg Ala Gly Val Thr Trp Gln His Gln
        25                  30                  35

CCA GAC AGT GGC CCG CCC GCT GCC GCC CCC GGC CAT CCC CTG GCC CCC        476
Pro Asp Ser Gly Pro Pro Ala Ala Ala Pro Gly His Pro Leu Ala Pro
    40                  45                  50

GGC CCT CAC CCG GCG GCG CCC TCC TCC TGG GGG CCC AGG CCC CGC CGC        524
Gly Pro His Pro Ala Ala Pro Ser Ser Trp Gly Pro Arg Pro Arg Arg
55                  60                  65                  70

TAC ACG GTG CTG AGC GTG GGT CCC GGA GGC CTG CGC AGC GGG AGG CTG        572
Tyr Thr Val Leu Ser Val Gly Pro Gly Gly Leu Arg Ser Gly Arg Leu
                75                  80                  85

CCC CTG CAG CCC CGC GTC CAG CTG GAT GAG CGC GGC CGG CAG CGC GGG        620
Pro Leu Gln Pro Arg Val Gln Leu Asp Glu Arg Gly Arg Gln Arg Gly
            90                  95                  100

GAC TTC TCG CTA TGG CTG CGC CCA GCC CGG CGC GCG GAC GCC GGC GAG        668
Asp Phe Ser Leu Trp Leu Arg Pro Ala Arg Arg Ala Asp Ala Gly Glu
        105                 110                 115

TAC CGC GCC GCG GTG CAC CTC AGG GAC CGC GCC CTC TCC TGC CGC CTC        716
Tyr Arg Ala Ala Val His Leu Arg Asp Arg Ala Leu Ser Cys Arg Leu
Tyr Arg Ala Ala Val His Leu Arg Asp Arg Ala Leu Ser Cys Arg Leu
    120                 125                 130

CGT CTG CGC CTG GGC CAG GCC TCG ATG ACT GCC AGC CCC CCA GGA TCT        764
Arg Leu Arg Leu Gly Gln Ala Ser Met Thr Ala Ser Pro Pro Gly Ser
135                 140                 145                 150

CTC AGA GCC TCC GAC TGG GTC ATT TTG AAC TGC TCC TTC AGC CGC CCT        812
Leu Arg Ala Ser Asp Trp Val Ile Leu Asn Cys Ser Phe Ser Arg Pro
                155                 160                 165

GAC CGC CCA GCC TCT GTG CAT TGG TTC CGG AAC CGG GGC CAG GGC CGA        860
Asp Arg Pro Ala Ser Val His Trp Phe Arg Asn Arg Gly Gln Gly Arg
            170                 175                 180

GTC CCT GTC CGG GAG TCC CCC CAT CAC CAC TTA GCG GAA AGC TTC CTC        908
Val Pro Val Arg Glu Ser Pro His His His Leu Ala Glu Ser Phe Leu
        185                 190                 195

TTC CTG CCC CAA GTC AGC CCC ATG GAC TCT GGG CCC TGG GGC TGC ATC        956
Phe Leu Pro Gln Val Ser Pro Met Asp Ser Gly Pro Trp Gly Cys Ile
    200                 205                 210

CTC ACC TAC AGA GAT GGC TTC AAC GTC TCC ATC ATG TAT AAC CTC ACT       1004
Leu Thr Tyr Arg Asp Gly Phe Asn Val Ser Ile Met Tyr Asn Leu Thr
215                 220                 225                 230

GTT CTG GGT CTG GAG CCC CCA ACT CCC TTG ACA GTG TAC GCT GGA GCA       1052
Val Leu Gly Leu Glu Pro Pro Thr Pro Leu Thr Val Tyr Ala Gly Ala
                235                 240                 245

GGT TCC AGG GTG GGG CTG CCC TGC CGC CTG CCT GCT GGT GTG GGG ACC       1100
Gly Ser Arg Val Gly Leu Pro Cys Arg Leu Pro Ala Gly Val Gly Thr
            250                 255                 260

CGG TCT TTC CTC ACT GCC AAG TGG ACT CCT CCT GGG GGA GGC CCT GAC       1148
Arg Ser Phe Leu Thr Ala Lys Trp Thr Pro Pro Gly Gly Gly Pro Asp
        265                 270                 275

CTC CTG GTG ACT GGA GAC AAT GGC GAC TTT ACC CTT CGA CTA GAG GAT       1196
Leu Leu Val Thr Gly Asp Asn Gly Asp Phe Thr Leu Arg Leu Glu Asp
    280                 285                 290

GTG AGC CAG GCC CAG GCT GGG ACC TAC ACC TGC CAT ATC CAT CTG CAG       1244
Val Ser Gln Ala Gln Ala Gly Thr Tyr Thr Cys His Ile His Leu Gln
295                 300                 305                 310

GAA CAG CAG CTC AAT GCC ACT GTC ACA TTG GCA ATC ATC ACA GTG ACT       1292
Glu Gln Gln Leu Asn Ala Thr Val Thr Leu Ala Ile Ile Thr Val Thr
                315                 320                 325
```

-continued

```
CCC AAA TCC TTT GGG TCA CCT GGA TCC CTG GGG AAG CTG CTT TGT GAG     1340
Pro Lys Ser Phe Gly Ser Pro Gly Ser Leu Gly Lys Leu Leu Cys Glu
        330                 335                 340

GTG ACT CCA GTA TCT GGA CAA GAA CGC TTT GTG TGG AGC TCT CTG GAC     1388
Val Thr Pro Val Ser Gly Gln Glu Arg Phe Val Trp Ser Ser Leu Asp
            345                 350                 355

ACC CCA TCC CAG AGG AGT TTC TCA GGA CCT TGG CTG GAG GCA CAG GAG     1436
Thr Pro Ser Gln Arg Ser Phe Ser Gly Pro Trp Leu Glu Ala Gln Glu
    360                 365                 370

GCC CAG CTC CTT TCC CAG CCT TGG CAA TGC CAG CTG TAC CAG GGG GAG     1484
Ala Gln Leu Leu Ser Gln Pro Trp Gln Cys Gln Leu Tyr Gln Gly Glu
375                 380                 385                 390

AGG CTT CTT GGA GCA GCA GTG TAC TTC ACA GAG CTG TCT AGC CCA GGT     1532
Arg Leu Leu Gly Ala Ala Val Tyr Phe Thr Glu Leu Ser Ser Pro Gly
                395                 400                 405

GCC CAA CGC TCT GGG AGA GCC CCA GGT GCC CTC CCA GCA GGC CAC CTC     1580
Ala Gln Arg Ser Gly Arg Ala Pro Gly Ala Leu Pro Ala Gly His Leu
            410                 415                 420

CTG CTG TTT CTC ACC CTT GGT GTC CTT TCT CTG CTC CTT TTG GTG ACT     1628
Leu Leu Phe Leu Thr Leu Gly Val Leu Ser Leu Leu Leu Leu Val Thr
        425                 430                 435

GGA GCC TTT GGC TTT CAC CTT TGG AGA AGA CAG TGG CGA CCA AGA CGA     1676
Gly Ala Phe Gly Phe His Leu Trp Arg Arg Gln Trp Arg Pro Arg Arg
440                 445                 450

TTT TCT GCC TTA GAG CAA GGG ATT CAC CCT CGC AGG CTC AGA GCA AGA     1724
Phe Ser Ala Leu Glu Gln Gly Ile His Pro Arg Arg Leu Arg Ala Arg
455                 460                 465                 470

TAGAGGAGCT GGAGCAAGAA CCGGAGCCGG AGCCGGAGCC GGAACCGGAG CCCGAGCCCG   1784

AGCCCGAGCC GGAGCAGCTC TGACCTGGAG CTGAGGCAGC AGCAGATCT CAGCAGCCCA    1844

GTCCAAATAA ACGTCCTGTC TAGCAGC                                       1871
```

(2) INFORMATION FOR SEQ ID NO:2:

(i) SEQUENCE CHARACTERISTICS:
        (A) LENGTH: 471 amino acids
        (B) TYPE: amino acid
        (D) TOPOLOGY: linear (ii) MOLECULE TYPE: protein (ix) FEATURE:
        (A) NAME/KEY: Peptide
        (B) LOCATION: 1
        (D) OTHER INFORMATION: /note= "Hydrogen is present at the
           N-terminus"

(xi) SEQUENCE DESCRIPTION: SEQ ID NO:2:

```
                                        Met Val Pro Val Val
                                          1                5

Trp Ala Gln Glu Gly Ala Pro Ala Gln Leu Pro Cys Ser Pro Thr Ile
                10                  15                  20

Pro Leu Gln Asp Leu Ser Leu Leu Arg Arg Ala Gly Val Thr Trp Gln
            25                  30                  35

His Gln Pro Asp Ser Gly Pro Pro Ala Ala Ala Pro Gly His Pro Leu
        40                  45                  50

Ala Pro Gly Pro His Pro Ala Ala Pro Ser Ser Trp Gly Pro Arg Pro
    55                  60                  65

Arg Arg Tyr Thr Val Leu Ser Val Gly Pro Gly Gly Leu Arg Ser Gly
70                  75                  80                  85

Arg Leu Pro Leu Gln Pro Arg Val Gln Leu Asp Glu Arg Gly Arg Gln
                90                  95                 100
```

```
Arg Gly Asp Phe Ser Leu Trp Leu Arg Pro Ala Arg Ala Asp Ala
            105                 110                 115
Gly Glu Tyr Arg Ala Ala Val His Leu Arg Asp Arg Ala Leu Ser Cys
            120                 125                 130
Arg Leu Arg Leu Arg Leu Gly Gln Ala Ser Met Thr Ala Ser Pro Pro
            135                 140                 145
Gly Ser Leu Arg Ala Ser Asp Trp Val Ile Leu Asn Cys Ser Phe Ser
150                 155                 160                 165
Arg Pro Asp Arg Pro Ala Ser Val His Trp Phe Arg Asn Arg Gly Gln
            170                 175                 180
Gly Arg Val Pro Val Arg Glu Ser Pro His His Leu Ala Glu Ser
            185                 190                 195
Phe Leu Phe Leu Pro Gln Val Ser Pro Met Asp Ser Gly Pro Trp Gly
            200                 205                 210
Cys Ile Leu Thr Tyr Arg Asp Gly Phe Asn Val Ser Ile Met Tyr Asn
            215                 220                 225
Leu Thr Val Leu Gly Leu Glu Pro Pro Thr Pro Leu Thr Val Tyr Ala
230                 235                 240                 245
Gly Ala Gly Ser Arg Val Gly Leu Pro Cys Arg Leu Pro Ala Gly Val
                250                 255                 260
Gly Thr Arg Ser Phe Leu Thr Ala Lys Trp Thr Pro Pro Gly Gly Gly
                265                 270                 275
Pro Asp Leu Leu Val Thr Gly Asp Asn Gly Asp Phe Thr Leu Arg Leu
            280                 285                 290
Glu Asp Val Ser Gln Ala Gln Ala Gly Thr Tyr Thr Cys His Ile His
            295                 300                 305
Leu Gln Glu Gln Gln Leu Asn Ala Thr Val Thr Leu Ala Ile Ile Thr
310                 315                 320                 325
Val Thr Pro Lys Ser Phe Gly Ser Pro Gly Ser Leu Gly Lys Leu Leu
                330                 335                 340
Cys Glu Val Thr Pro Val Ser Gly Gln Glu Arg Phe Val Trp Ser Ser
                345                 350                 355
Leu Asp Thr Pro Ser Gln Arg Ser Phe Ser Gly Pro Trp Leu Glu Ala
            360                 365                 370
Gln Glu Ala Gln Leu Leu Ser Gln Pro Trp Gln Cys Gln Leu Tyr Gln
            375                 380                 385
Gly Glu Arg Leu Leu Gly Ala Ala Val Tyr Phe Thr Glu Leu Ser Ser
390                 395                 400                 405
Pro Gly Ala Gln Arg Ser Gly Arg Ala Pro Gly Ala Leu Pro Ala Gly
            410                 415                 420
His Leu Leu Leu Phe Leu Thr Leu Gly Val Leu Ser Leu Leu Leu Leu
            425                 430                 435
Val Thr Gly Ala Phe Gly Phe His Leu Trp Arg Arg Gln Trp Arg Pro
            440                 445                 450
Arg Arg Phe Ser Ala Leu Glu Gln Gly Ile His Pro Arg Arg Leu Arg
            455                 460                 465
Ala Arg
470

(2) INFORMATION FOR SEQ ID NO:3:

(i) SEQUENCE CHARACTERISTICS:
        (A) LENGTH: 30 amino acids
        (B) TYPE: amino acid
        (D) TOPOLOGY: linear
```

(xi) SEQUENCE DESCRIPTION: SEQ ID NO:3:

```
Gly Pro Pro Ala Ala Ala Pro Gly His Pro Leu Ala Pro Gly Pro His
 1               5                  10                  15

Pro Ala Ala Pro Ser Ser Trp Gly Pro Arg Pro Arg Arg Tyr
             20                  25
```

(2) INFORMATION FOR SEQ ID NO:4:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (xi) SEQUENCE DESCRIPTION: SEQ ID NO:4:

```
CCTGCAATGT CATTCTTTGA GCTCAGTTCC TCATCTCTGT CATGGAGAGC ATTAGATTTC     60
ATGAATTCAT ACTAAGTGTC CAATACAGTG CTTAGCACGT AATGAAGCCT CAATACAATG    120
TAGTTATTCT CCATGCCCCA CAAAGCTGCA TGCCTAGCCT CAGACCTACC ATTTTTTGGG    180
GTGCAGTAAG GCTTCCTGTC CACCATGTTC CCAGGGACAT TGTACTGATG GGTGGAAAGG    240
CAGGTCTAAA GGGGTCACGA AGTTCTGGGA GGTTAAGGGA ACGAGGAAGG AGATTGAGCA    300
ACAAGGAAAG AGCTTGCCAA GAAGGAGGTG TGAATATTGG GACTGAGGAG GCAGCTTAGA    360
GATGGGCAAG GGGGCAGTTC CAGGCAGAAA TGGTTCGTGG AGGCAGAAGG TCCCTGGGAG    420
AGGGAGCAGT CTGGAGGGTG GGCAGGGGC GAGGAGGGGG AGGTGGGGAG ACCCAGGACT    480
GAGGAAGTAA ACAAGGGGAG CGCCACCACA GAGGTGGAGA GGTGGAGGGT GCTGCTGCTG    540
GGAATCAACC CCCTCAGACT TTCCACTGCG AAGCGAAACC GTAAGCCCTG GGGTGCGGGG    600
GGCGGGCCGG GAGGAGGGGA AGTGGGGAAG GTGGAGGGAA GGCCGGGCAC AGGGGTGAAG    660
GCCCAGAGAC CAGCAGAACG GCATCCCAGC CACGACGGCC ACTTTGCTCT GTCTGCTGTC    720
CGCCACGGCC CTGCTCTGTT CCCTGGGACA CCCCCGCCCC CACCTCCTCA GGCTGCCTGA    780
TCTGCCCAGC TTTCCAGCTT TCCTCTGGAT TCCGGCCTCT GGTCATCCCT CCCCACCCTC    840
TCTCCAAGGC CCTCTCCTGG TCTCCCTTCT TCTAGAACCC CTTCCTCCAC CTCCCTCTCT    900
GCAGAACTTC TCCTTTCCCC CCACCCCCCA CCACTGCCCC CTTTCCTTTT CTGACCTCCT    960
TTTGGAGGGC TCAGCGCTGC CCAGACCATA GGAGAGATG                          999
```

(2) INFORMATION FOR SEQ ID NO:5:

(i) SEQUENCE CHARACTERISTICS:
        (A) LENGTH: 1164 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 22..1161

(xi) SEQUENCE DESCRIPTION: SEQ ID NO:5:

```
GCTGCCCAGA CCATAGGAGA G ATG TGG GAG GCT CAG TTC CTG GGC TTG CTG      51
                       Met Trp Glu Ala Gln Phe Leu Gly Leu Leu
                         1               5                  10

TTT CTG CAG CCG CTT TGG GTG GCT CCA GTG AAG CCT CTC CAG CCA GGG      99
Phe Leu Gln Pro Leu Trp Val Ala Pro Val Lys Pro Leu Gln Pro Gly
             15                  20                  25

GCT GAG GTC CCG GTG GTG TGG GCC CAG GAG GGG GCT CCT GCC CAG CTC     147
Ala Glu Val Pro Val Val Trp Ala Gln Glu Gly Ala Pro Ala Gln Leu
         30                  35                  40
```

```
CCC TGC AGC CCC ACA ATC CCC CTC CAG GAT CTC AGC CTT CTG CGA AGA     195
Pro Cys Ser Pro Thr Ile Pro Leu Gln Asp Leu Ser Leu Leu Arg Arg
        45                  50                  55

GCA GGG GTC ACT TGG CAG CAT CAG CCA GAC AGT GGC CCG CCC GCT GCC     243
Ala Gly Val Thr Trp Gln His Gln Pro Asp Ser Gly Pro Pro Ala Ala
    60                  65                  70

GCC CCC GGC CAT CCC CTG GCC CCC GGC CCT CAC CCG GCG GCG CCC TCC     291
Ala Pro Gly His Pro Leu Ala Pro Gly Pro His Pro Ala Ala Pro Ser
75                  80                  85                  90

TCC TGG GGG CCC AGG CCC CGC CGC TAC ACG GTG CTG AGC GTG GGT CCC     339
Ser Trp Gly Pro Arg Pro Arg Arg Tyr Thr Val Leu Ser Val Gly Pro
                95                  100                 105

GGA GGC CTG CGC AGC GGG AGG CTG CCC CTG CAG CCC CGC GTC CAG CTG     387
Gly Gly Leu Arg Ser Gly Arg Leu Pro Leu Gln Pro Arg Val Gln Leu
            110                 115                 120

GAT GAG CGC GGC CGG CAG CGC GGG GAC TTC TCG CTA TGG CTG CGC CCA     435
Asp Glu Arg Gly Arg Gln Arg Gly Asp Phe Ser Leu Trp Leu Arg Pro
        125                 130                 135

GCC CGG CGC GCG GAC GCC GGC GAG TAC CGC GCC GCG GTG CAC CTC AGG     483
Ala Arg Arg Ala Asp Ala Gly Glu Tyr Arg Ala Ala Val His Leu Arg
    140                 145                 150

GAC CGC GCC CTC TCC TGC CGC CTC CGT CTG CGC CTG GGC CAG GCC TCG     531
Asp Arg Ala Leu Ser Cys Arg Leu Arg Leu Arg Leu Gly Gln Ala Ser
155                 160                 165                 170

ATG ACT GCC AGC CCC CCA GGA TCT CTC AGA GCC TCC GAC TGG GTC ATT     579
Met Thr Ala Ser Pro Pro Gly Ser Leu Arg Ala Ser Asp Trp Val Ile
                175                 180                 185

TTG AAC TGC TCC TTC AGC CGC CCT GAC CGC CCA GCC TCT GTG CAT TGG     627
Leu Asn Cys Ser Phe Ser Arg Pro Asp Arg Pro Ala Ser Val His Trp
            190                 195                 200

TTC CGG AAC CGG GGC CAG GGC CGA GTC CCT GTC CGG GAG TCC CCC CAT     675
Phe Arg Asn Arg Gly Gln Gly Arg Val Pro Val Arg Glu Ser Pro His
        205                 210                 215

CAC CAC TTA GCG GAA AGC TTC CTC TTC CTG CCC CAA GTC AGC CCC ATG     723
His His Leu Ala Glu Ser Phe Leu Phe Leu Pro Gln Val Ser Pro Met
    220                 225                 230

GAC TCT GGG CCC TGG GGC TGC ATC CTC ACC TAC AGA GAT GGC TTC AAC     771
Asp Ser Gly Pro Trp Gly Cys Ile Leu Thr Tyr Arg Asp Gly Phe Asn
235                 240                 245                 250

GTC TCC ATC ATG TAT AAC CTC ACT GTT CTG GGT CTG GAG CCC CCA ACT     819
Val Ser Ile Met Tyr Asn Leu Thr Val Leu Gly Leu Glu Pro Pro Thr
                255                 260                 265

CCC TTG ACA GTG TAC GCT GGA GCA GGT TCC AGG GTG GGG CTG CCC TGC     867
Pro Leu Thr Val Tyr Ala Gly Ala Gly Ser Arg Val Gly Leu Pro Cys
            270                 275                 280

CGC CTG CCT GCT GGT GTG GGG ACC CGG TCT TTC CTC ACT GCC AAG TGG     915
Arg Leu Pro Ala Gly Val Gly Thr Arg Ser Phe Leu Thr Ala Lys Trp
        285                 290                 295

ACT CCT CCT GGG GGA GGC CCT GAC CTC CTG GTG ACT GGA GAC AAT GGC     963
Thr Pro Pro Gly Gly Gly Pro Asp Leu Leu Val Thr Gly Asp Asn Gly
    300                 305                 310

GAC TTT ACC CTT CGA CTA GAG GAT GTG AGC CAG GCC CAG GCT GGG ACC     1011
Asp Phe Thr Leu Arg Leu Glu Asp Val Ser Gln Ala Gln Ala Gly Thr
315                 320                 325                 330

TAC ACC TGC CAT ATC CAT CTG CAG GAA CAG CAG CTC AAT GCC ACT GTC     1059
Tyr Thr Cys His Ile His Leu Gln Glu Gln Gln Leu Asn Ala Thr Val
                335                 340                 345

ACA TTG GCA ATC ATC ACA GTG ACT CCC AAA TCC TTT GGG TCA CCT GGA     1107
Thr Leu Ala Ile Ile Thr Val Thr Pro Lys Ser Phe Gly Ser Pro Gly
            350                 355                 360
```

```
TCC TTT CCT GGG ACC CGG CAA GAA CCA AAA ACT CAC TCT CTT CAA GGA     1155
Ser Phe Pro Gly Thr Arg Gln Glu Pro Lys Thr His Ser Leu Gln Gly
    365                 370                 375

AAT CCG TAA                                                          1164
Asn Pro
    380

(2) INFORMATION FOR SEQ ID NO:6:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:6:

Met Trp Glu Ala Gln Phe Leu Gly Leu Leu Phe Leu Gln Pro Leu Trp
 1               5                  10                  15

Val Ala Pro Val Lys Pro Leu Gln Pro Gly Ala Glu Val Pro Val Val
             20                  25                  30

Trp Ala Gln Glu Gly Ala Pro Ala Gln Leu Pro Cys Ser Pro Thr Ile
         35                  40                  45

Pro Leu Gln Asp Leu Ser Leu Leu Arg Arg Ala Gly Val Thr Trp Gln
     50                  55                  60

His Gln Pro Asp Ser Gly Pro Pro Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320
```

```
Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Phe Pro Gly Thr Arg
                355                 360                 365

Gln Glu Pro Lys Thr His Ser Leu Gln Gly Asn Pro
    370                 375                 380

(2) INFORMATION FOR SEQ ID NO:7:

(i) SEQUENCE CHARACTERISTICS:
        (A) LENGTH: 470 amino acids
        (B) TYPE: amino acid
        (D) TOPOLOGY: linear (xi) SEQUENCE DESCRIPTION: SEQ ID NO:7:

Val Pro Val Val
                                         1

Trp Ala Gln Glu Gly Ala Pro Ala Gln Leu Pro Cys Ser Pro Thr Ile
 5                  10                  15                  20

Pro Leu Gln Asp Leu Ser Leu Leu Arg Arg Ala Gly Val Thr Trp Gln
                25                  30                  35

His Gln Pro Asp Ser Gly Pro Ala Ala Ala Pro Gly His Pro Leu
                40                  45                  50

Ala Pro Gly Pro His Pro Ala Ala Pro Ser Ser Trp Gly Pro Arg Pro
                55                  60                  65

Arg Arg Tyr Thr Val Leu Ser Val Gly Pro Gly Gly Leu Arg Ser Gly
            70                  75                  80

Arg Leu Pro Leu Gln Pro Arg Val Gln Leu Asp Glu Arg Gly Arg Gln
 85                 90                  95                  100

Arg Gly Asp Phe Ser Leu Trp Leu Arg Pro Ala Arg Arg Ala Asp Ala
                105                 110                 115

Gly Glu Tyr Arg Ala Ala Val His Leu Arg Asp Arg Ala Leu Ser Cys
                120                 125                 130

Arg Leu Arg Leu Arg Leu Gly Gln Ala Ser Met Thr Ala Ser Pro Pro
135                 140                 145

Gly Ser Leu Arg Ala Ser Asp Trp Val Ile Leu Asn Cys Ser Phe Ser
150                 155                 160

Arg Pro Asp Arg Pro Ala Ser Val His Trp Phe Arg Asn Arg Gly Gln
165                 170                 175                 180

Gly Arg Val Pro Val Arg Glu Ser Pro His His Leu Ala Glu Ser
                185                 190                 195

Phe Leu Phe Leu Pro Gln Val Ser Pro Met Asp Ser Gly Pro Trp Gly
                200                 205                 210

Cys Ile Leu Thr Tyr Arg Asp Gly Phe Asn Val Ser Ile Met Tyr Asn
                215                 220                 225

Leu Thr Val Leu Gly Leu Glu Pro Pro Thr Pro Leu Thr Val Tyr Ala
                230                 235                 240

Gly Ala Gly Ser Arg Val Gly Leu Pro Cys Arg Leu Pro Ala Gly Val
245                 250                 255                 260

Gly Thr Arg Ser Phe Leu Thr Ala Lys Trp Thr Pro Pro Gly Gly Gly
                265                 270                 275

Pro Asp Leu Leu Val Thr Gly Asp Asn Gly Asp Phe Thr Leu Arg Leu
                280                 285                 290
```

```
Glu Asp Val Ser Gln Ala Gln Ala Gly Thr Tyr Thr Cys His Ile His
            295                 300                 305

Leu Gln Glu Gln Gln Leu Asn Ala Thr Val Thr Leu Ala Ile Ile Thr
    310                 315                 320

Val Thr Pro Lys Ser Phe Gly Ser Pro Gly Ser Leu Gly Lys Leu Leu
325                 330                 335                 340

Cys Glu Val Thr Pro Val Ser Gly Gln Glu Arg Phe Val Trp Ser Ser
                345                 350                 355

Leu Asp Thr Pro Ser Gln Arg Ser Phe Ser Gly Pro Trp Leu Glu Ala
            360                 365                 370

Gln Glu Ala Gln Leu Leu Ser Gln Pro Trp Gln Cys Gln Leu Tyr Gln
    375                 380                 385

Gly Glu Arg Leu Leu Gly Ala Ala Val Tyr Phe Thr Glu Leu Ser Ser
390                 395                 400

Pro Gly Ala Gln Arg Ser Gly Arg Ala Pro Gly Ala Leu Pro Ala Gly
405                 410                 415                 420

His Leu Leu Leu Phe Leu Thr Leu Gly Val Leu Ser Leu Leu Leu Leu
                425                 430                 435

Val Thr Gly Ala Phe Gly Phe His Leu Trp Arg Arg Gln Trp Arg Pro
                440                 445                 450

Arg Arg Phe Ser Ala Leu Glu Gln Gly Ile His Pro Arg Arg Leu Arg
            455                 460                 465

Ala Arg
    470

(2) INFORMATION FOR SEQ ID NO:8:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Cys Arg Gly Phe Ser Phe Arg His Leu Leu Pro Leu Leu Leu Leu
    1               5                   10                  15

Gln Leu Ser Lys Leu Val Val Thr Gln Gly Lys Thr Val Val Leu
                20                  25                  30

Gly Lys Glu Gly Gly Ser Ala Glu Leu Pro Cys Glu Ser Thr Ser Arg
                35                  40                  45

Arg Ser Ala Ser Phe Ala Trp Lys Ser Asp Gln Lys Thr Ile Leu
        50                  55                  60

Gly Tyr Lys Asn Lys Leu Leu Ile Lys Gly Ser Leu Glu Leu Tyr Ser
    65                  70                  75                  80

Arg Phe Asp Ser Arg Lys Asn Ala Trp Glu Arg Gly Ser Phe Pro Leu
                85                  90                  95

Ile Ile Asn Lys Leu Arg Met Glu Asp Ser Gln Thr Tyr Val Cys Glu
                100                 105                 110

Leu Glu Asn Lys Lys Glu Glu Val Glu Leu Trp Val Phe Arg Val Thr
                115                 120                 125

Phe Asn Pro Gly Thr Arg Leu Leu Gln Gly Gln Ser Leu Thr Leu Ile
            130                 135                 140

Leu Asp Ser Asn Pro Lys Val Ser Asp Pro Ile Glu Cys Lys His
    145                 150                 155                 160

Lys Ser Ser Asn Ile Val Lys Asp Ser Lys Ala Phe Ser Thr His Ser
```

```
                    165                 170                 175
Leu Arg Ile Gln Asp Ser Gly Ile Trp Asn Cys Thr Val Thr Leu Asn
            180                 185                 190
Gln Lys Lys His Ser Phe Asp Met Lys Leu Ser Val Leu Gly Phe Ala
        195                 200                 205
Ser Thr Ser Ile Thr Ala Tyr Lys Ser Glu Gly Glu Ser Ala Glu Phe
    210                 215                 220
Ser Phe Pro Leu Asn Leu Gly Glu Ser Leu Gln Gly Glu Leu Arg
225                 230                 235                 240
Trp Lys Ala Glu Lys Ala Pro Ser Ser Gln Ser Trp Ile Thr Phe Ser
            245                 250                 255
Leu Lys Asn Gln Lys Val Ser Val Gln Lys Ser Thr Ser Asn Pro Lys
        260                 265                 270
Phe Gln Leu Ser Glu Thr Leu Pro Leu Thr Leu Gln Ile Pro Gln Val
    275                 280                 285
Ser Leu Gln Phe Ala Gly Ser Gly Asn Leu Thr Leu Thr Leu Asp Arg
290                 295                 300
Gly Ile Leu Tyr Gln Glu Val Asn Leu Val Val Met Lys Val Thr Gln
305                 310                 315                 320
Pro Asp Ser Asn Thr Leu Thr Cys Glu Val Met Gly Pro Thr Ser Pro
            325                 330                 335
Lys Met Arg Leu Ile Leu Lys Gln Glu Asn Gln Glu Ala Arg Val Ser
        340                 345                 350
Arg Gln Glu Lys Val Ile Gln Val Gln Ala Pro Glu Ala Gly Val Trp
    355                 360                 365
Gln Cys Leu Leu Ser Glu Gly Glu Val Lys Met Asp Ser Lys Ile
370                 375                 380
Gln Val Leu Ser Lys Gly Leu Asn Gln Thr Met Phe Leu Ala Val Val
385                 390                 395                 400
Leu Gly Ser Ala Phe Ser Phe Leu Val Phe Thr Gly Leu Cys Ile Leu
            405                 410                 415
Phe Cys Val Arg Cys Arg His Gln Gln Arg Gln Ala Ala Arg Met Ser
        420                 425                 430
Gln Ile Lys Arg Leu Leu Ser Glu Lys Lys Thr Cys Gln Cys Ser His
    435                 440                 445
Arg Met Gln Lys Ser His Asn Leu Ile
450                 455
```

(2) INFORMATION FOR SEQ ID NO:9:

(i) SEQUENCE CHARACTERISTICS:
        (A) LENGTH: 498 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Trp Glu Ala Gln Phe Leu Gly Leu Leu Phe Leu Gln Pro Leu Trp
1               5                   10                  15
Val Ala Pro Val Lys Pro Leu Gln Pro Gly Ala Glu Val Pro Val Val
            20                  25                  30
Trp Ala Gln Glu Gly Ala Pro Ala Gln Leu Pro Cys Ser Pro Thr Ile
        35                  40                  45
Pro Leu Gln Asp Leu Ser Leu Leu Arg Arg Ala Gly Val Thr Trp Gln
    50                  55                  60
```

```
His Gln Pro Asp Ser Gly Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Arg Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Thr Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Arg Arg Leu Arg
```

```
                     485                  490                  495
         Ala Arg (2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Asp Gly Tyr Cys
    1

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:11:

GGAAGATCTT CC                                                          12
```

PROTEINS PRODUCED BY HUMAN LYMPHOCYTES DNA SEQUENCE ENCODING THESE PROTEINS AND THEIR PHARMACEUTICAL AND BIOLOGICAL USES

This application is a continuation of application Ser. No. 07/922,466, filed Jul. 10, 1992, abandoned, which is a CIP of application Ser. No. 07/854,644, filed Sep. 8, 1992, abandoned, which is a continuation of U.S. National Phase of PCT/FR91/00009 filed Jan. 8, 1991.

BACKGROUND OF THE INVENTION

1. Field of the Invention

The present invention relates to proteins produced by human lymphocytes and, in particular, to a protein expressed at the surface of the latter, DNA sequences coding for these proteins and the pharmaceutical and biological uses of these proteins.

2. Description of the Related Art

A certain number of protein structures of the cell surface "belong" to the "superfamily" of the immunoglobulins (IgSF). This family of molecules includes the proteins comprising at least one domain with a characteristic folding region called the Ig fold. Several of these molecules have essential functions in immune responses.

In addition to ensuring specific antigen recognition, as do for example the immunoglobulins and the T receptors, they may function as monomorphic ligands critical in cell-cell interactions (for example ICAM, CD4, CD8), receptors for viruses (for example CD4, ICAM) or receptors for the lymphokines (for example IL1-R, IL6-R).

The discovery and characterization of the membrane proteins expressed on the lymphocytes have been facilitated by the development of genetic engineering techniques. By means of various experimental techniques, this methodology makes it possible to characterize the genes coding for the proteins and hence to deduce the peptide sequence from knowledge of the nucleotide sequence of the gene. Other applications of these genetic engineering techniques based on the same experimental principles enable virtually unlimited quantities of the proteins corresponding to the genes which have been discovered to be produced as a consequence of procaryotic or eucaryotic systems of expression.

SUMMARY OF THE INVENTION

The inventors have attempted to discover novel genes coding for hitherto undescribed membrane proteins.

The development of the experiments of the inventors has led to the isolation of a novel complementary cDNA designated FDC from natural cytotoxic lymphocytes. This cDNA codes for a protein called LAG-3 (for Lymphocyte Activation Gene-3) which possesses a signal sequence which is thought to be removed to generate the mature protein.

Consequently, the present invention relates to a DNA sequence comprising the nucleotide sequence designated FDC, corresponding to the cDNA sequence represented in the sequence SEQ ID No. 1.

Translation starts at nucleotide 231 and ends at nucleotide 1724.

The present invention also relates to the protein encoded by FDC, namely the protein LAG-3 represented in the sequence ID No: 9 (protein sequence −28 to 470 renumbered 1 to 498).

The first 28 amino acids should constitute a signal sequence which has been removed in the mature protein.

Hence, the present invention relates more particularly to the protein corresponding to the protein sequence 1 to 470 of SEQ ID No: 7.

The mature protein constitutes a membrane protein of type I of 470 amino acids, the theoretical molecular mass of which deduced from the protein structure is 51295 daltons and the isoelectric point is 10.9. It comprises an extra-cellular region containing about 420 amino acids and a cytoplasmic region containing about 24 amino acids linked by a transmembrane peptide containing about 26 amino acids. The extra-cellular part of the LAG-3 protein corresponds to the amino acids 1 to 420 of the LAG-3 protein described above.

Comparison of the sequence of the LAG-3 gene represented by the cDNA FDC above as well as the exon/intron organisation of the LAG-3 gene with those of other molecules of the Ig/SF type has revealed a close relationship of the LAG-3 protein with the CD4 protein.

It is known that the genes of eucaryotic cells exhibit the phenomenon of polytypy. As a result of this phenomenon, some of the amino acids of the coded protein are sometimes replaced without modification of the activity. The present invention includes the proteins resulting from this phenomenon.

Hence, the present invention relates more generally to a protein having the peptide sequence corresponding to the sequence SEQ ID No. 2, SEQ ID No:7, SEQ ID No:9 and the sequences which differ from it by one or more amino acids and which possess the same activity.

Furthermore, the inventors have found a DNA sequence which is a promoter region for a gene coding for a protein according to the invention. This sequence is that represented in sequence SEQ ID No. 4.

Consequently, the present invention also relates to this DNA sequence.

The present invention also relates to a DNA sequence comprising the promoter DNA sequence as defined above and a DNA sequence coding for a protein according to the present invention.

In the present invention, the inventors first isolated an FDC complementary DNA by means of the following operations.

- culture of lymphocyte cells known as natural cytotoxic cells
- isolation from these lymphocytes of the messenger RNA bound to the membranes of the intracellular endoplasmic reticulum
- isolation of the single-stranded complementary DNA from the messenger RNA, then of the double-stranded complementary DNA
- insertion in a vector such as the bacteriophage lambda gt10
- preparation of a single-stranded DNA probe from the messenger RNA of the cells and purification by means of a subtraction-hybridization technique so as to select the copies of the RNAs present in the natural cytotoxic lymphocyte cells and absent from other transformed hematopoietic cells.
- selection of the complementary DNAs inserted into the vector which react with the probe
- transfer of the DNA selected into a plasmid vector in order to amplify, purify and sequence it.

The protein sequence according to the invention was obtained by:

translation of the nucleotide sequence of the FDC cDNA.

The existence of this protein in the natural state on T cells was demonstrated by:

preparation of sera directed against a synthetic peptide representing a region probably exposed toward the exterior of the product of translation of the FDC cDNA which has a protein structure in the form of a loop, immunoprecipitation of the LAG-3 protein by anti-peptide hetero-antibodies.

The proteins according to the invention may also be obtained by other methods of purification of membrane proteins or by classical peptide synthesis or also by application of genetic engineering techniques comprising the insertion of a DNA sequence coding for a protein according to the invention into an expression vector such as a plasmid and the transformation of cells with this expression vector and the culture of these cells.

Hence, the present invention also relates to plasmids and expression vectors comprising a DNA sequence coding for a protein according to the invention as well as hosts transformed with this vector.

The present invention also relates to a therapeutic composition containing as active ingredient a protein according to the invention or a part of this protein, in particular the soluble part corresponding to the extracellular region of the protein extending from amino acid 1 to amino acid 420 of the protein sequence previously described or a part of this extracellular region and, in particular, all or part of at least one of the four extracellular domains of the immunoglobulin type of the LAG-3 protein (sequences 1 to 142, 143 to 232, 233 to 342 and 343 to 413). The part of the protein may also be constituted by all or part of the cytoplasmic region (sequence 450 to 470). The extracellular part may, in particular, be the sequence represented in the sequence SEQ ID No. 3.

This therapeutic composition is active in the treatment of certain diseases implicating the immune system in which the binding of the ligand(s) of the LAG-3 protein to this protein causes the transmission of signals into the interior of the cell, or modifications of cellular interactions.

In this case, the composition according to the invention may act by binding the ligand(s) of the membrane protein LAG-3, thus preventing the detrimental binding of this ligand or these ligands to the LAG-3 protein by a phenomenon of competitive inhibition.

The present invention also relates to monoclonal antibodies directed against a protein according to the invention or an immunogenic sequence of such a protein, in particular a peptide sequence comprising the sequence represented in SEQ No. 3.

The present invention also relates to hybridomas producing such monoclonal antibodies.

The present invention also includes the fragments and derivatives of the monoclonal antibodies according to the invention which react with defined regions of the LAG-3 protein. Such fragments are, in particular, the F(ab')$_2$ fragments which may be obtained by enzymatic cleavage of the antibody molecules with pepsin, the Fab' fragments which may be obtained by reduction of the disulfide bridges of the F(ab')$_2$ fragments and the Fab fragments which may be obtained by enzymatic cleavage of the antibody molecules with papain in the presence of a reducing agent. These fragments as well as Fv fragments may also be obtained by genetic engineering.

The monoclonal antibody derivatives are, for example, antibodies or fragments of these antibodies to which markers such as a radioisotope are linked. The monoclonal antibody derivatives are also antibodies of fragments of these antibodies to which therapeutically active molecules, in particular cytotoxic substances, are linked.

Furthermore, the monoclonal antibodies or the soluble fractions of the LAG-3 protein and, in particular, all or part of at least one of the four extracellular domains of the immunoglobulin type of the LAG-3 protein (sequences 1 to 142, 143 to 232, 233 to 342 and 342 to 413) or the cytoplasmic region (sequences 450 to 470) of this protein may be used in the treatment of human diseases due to infection by viruses of the HIV type.

These same products may be used in the treatment of human diseases in which a pathophysiological mechanism causes intercellular adhesion interactions between a ligand and LAG-3 (in particular with the first and/or second external domain of LAG-3) such as, for example, the auto-immune diseases.

They may also be used in the treatment of the human diseases caused by viruses binding specifically to the LAG-3 molecule and, in particular, to the first, NH$_2$-terminal external domain.

The present invention also relates to a dosing or identification method for the proteins according to the invention which comprises the use of the monoclonal antibodies according to the invention.

For this purpose it is possible to use, in the case in which a part of the LAG-3 protein is soluble in the native state, a radio-immunological method of the RIA type or the IRMA type (technique of the sandwich type using a cold antigen and competition between a cold antibody and a labelled antibody) or an immuno-enzymatic method of the ELISA type or the IEMA type (technique of the sandwich type).

In order to identify the LAG-3 protein bound to the membrane, it is possible to use methods such as direct immunofluorescence (using anti-LAG-3 antibodies labelled with a fluorescent substance) or indirect immunofluorescent (by using a labelled anti-Ig mouse immunoglobulin in the case in which the anti-LAG-3 antibodies have been produced in this species).

The monoclonal antibodies directed against the proteins according to the invention or fractions of them may be prepared according to a standard method. For this purpose, the protein fractions may be coupled if necessary to an immunogenic agent such as tetanus toxoid by means of a coupling agent such as glutaraldehyde.

A more detailed description will be given hereafter of the isolation of the FDC cDNA and the LAG-3 gene coding for the protein by referring to the appended Figures.

BRIEF DESCRIPTION OF THE DRAWINGS

FIG. 5 presents the alignment of the domains 1 and 2 (corresponding to amino acid residues 119 to 264 of SEQ ID NO:9) with the domains 3 and 4 (corresponding to amino acid residues 304 to 435 of SEQ ID NO:9) of the LAG-3 protein;

FIG. 6 presents the alignment of the peptide sequences of LAG-3 (SEQ ID NO:9) and the CD4 (SEQ ID NO:8) protein of the rat;

FIG. 15, graph 2 shows that no inhibition was observed with the isotype matched (IgG1) anti-CD4 mAb, OKT4E;

DESCRIPTION OF THE PREFERRED EMBODIMENTS

Figure 1:
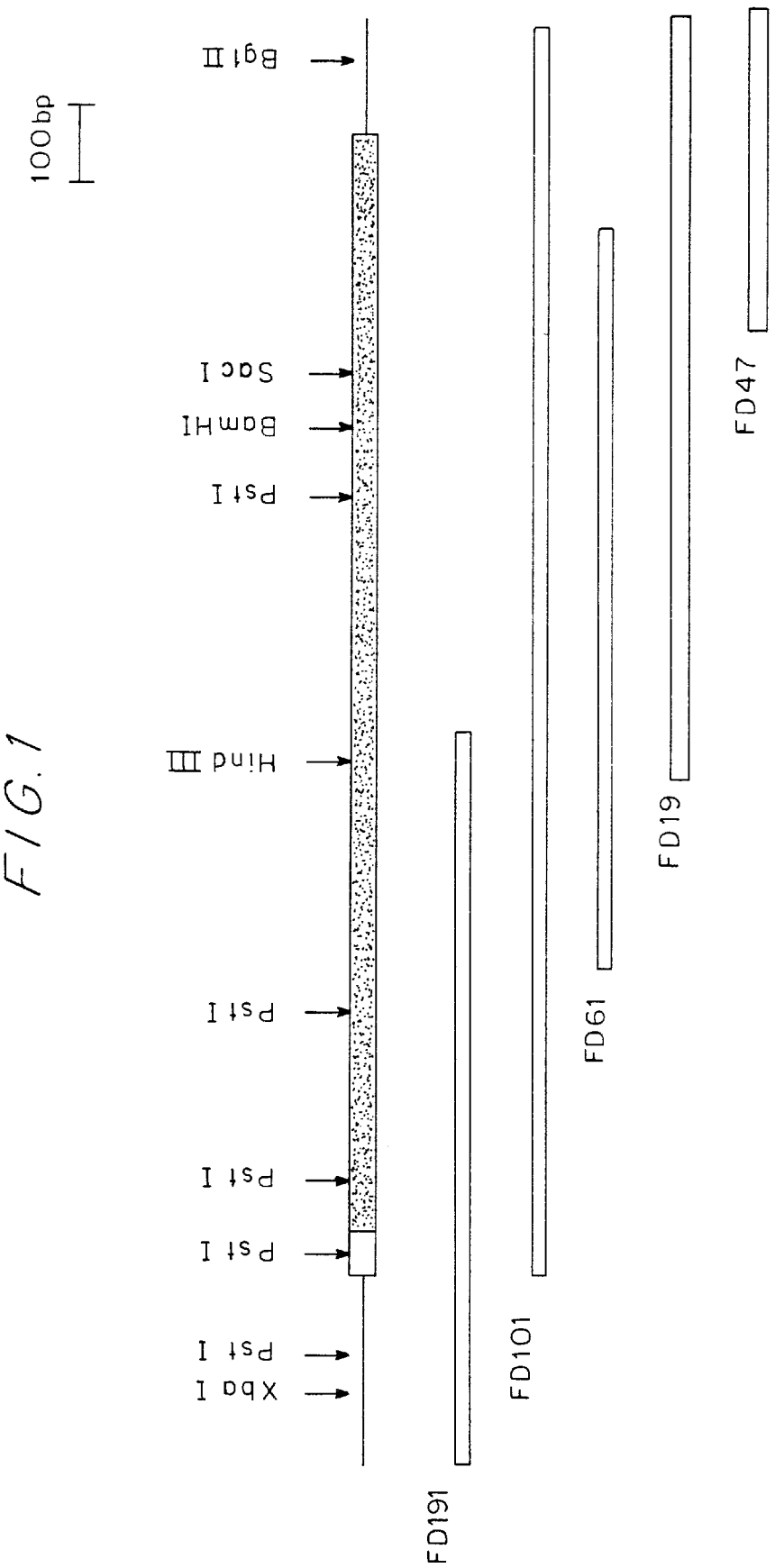
FIG. 1 presents the restriction map of the FDC cDNA and the clones of cDNA which have enabled the sequence of the FDC clone to be determined.

I—Culture and preparation of the mRNA linked to the membranes of the endoplasmic reticulum.

The isolation and the characteristics of the fetal clone, F55IIIE5 (phenotype CD3$^-$ CD2$^+$) have been previously described by Nowill et al (1).

The mass culture was carried out in the presence of recombinant interleukin-2 and the supernatant of lymphocyte-conditioned medium on a feeder substratum of allogenic irradiated mononucleated blood cells and a cell line transformed by the EBV virus (called LAZ 388) on V-bottomed 96-well plates. 3000 cells were placed in each well at day 0. The pooling of 200 plates with $3 \times 10^6$ cells per ml at day 12 gave a harvest of $6 \times 10^9$ cells.

The preparation of the cytoplasmic RNAs, the RNAs bound to the membranes of the endoplasmic reticulum and the mRNAs was performed by introducing some modifications to the methods described by Maniatis (2), Mechler (3) and Aviv (4). Thus, $4 \times 10^9$ F55IIIE5 cells were loaded onto sucrose gradients after hypotonic shock and mechanical grinding according to the method described by Mechler. The cytoplasmic RNAs borne by the ribosomes bound to the membranes of the endoplasmic reticulum were purified between sucrose gradients. This makes it possible to work subsequently with mRNAs which have a signal sequence and which consequently code for proteins borne by the membrane or secreted into the internal part of the ergastoplasm (and towards the exterior of the cell). This method of isolation of RNA of the so-called MB (membrane-bound) type makes it possible to remove right away about 90% of the transcribed genes which code for intracellular proteins incapable of being secreted towards the exterior or transported towards the membrane and, consequently, of no interest in the context of the invention. In addition to the isolation of the MB-F55IIIE5 mRNA which serves as substrate for the construction of the library, on the one hand, and the preparation of the probe, on the other, the methods of purification described by Aviv (4), Maniatis (2) and Triebel (5) made possible the isolation of RNAs of the various clones and cell lines which are used and mRNAs of Jurkat, U937, Laz388 and K562 cells (about $10^9$ cells of each line) which are used to subtract the probe.

These methods comprise:

A—Preparation of the cytoplasmic RNA.

1 ml of lysis buffer (50 mM Tris HCl, 62.5 mM EDTA, 0.4% TRITON X-100, surfactant 2.5M LiCl) is added to a vial containing 20 to $30 \times 10^6$ cells as a dry pellet. After gentle dissolution of the pellet, the lysis buffer is transferred to cold EPPENDORF tubes containing 50 µl of 10% NP40.

After 5 minutes on ice, the tubes are centrifuged for 1 min at 8000 rev/min. The supernatant (RNA) is removed and introduced into FALCON tubes containing 1 ml of phenol, 1 ml of CHCl$_3$, 1 ml of STE 2% SDS (150 mM NaCl, 10 mM Tris, 1 mM MgCl$_2$, 2% SDS). The tubes are centrifuged for 10 min. at 5000 rev/min. The upper phase is removed, 1 ml of phenol and 1 ml of chloroform are added. After centrifugation for 5 min. at 5000 rev/min., the upper phase is removed. 100 µl of 0.2M EDTA, 200 µl of 3M NaAc and 5 ml of ethanol are added. The mixture is left at −20° C. overnight before being centrifuged for 30 min at 10000 rev/min. The pellet is dried. It is taken up in 400 µl of cold 0.3M NaAc. 1 ml of ethanol is added to the FALCON tube. The ethanol is transferred to the EPPENDORF tube, the mixture is left for 1 h at −20° C. The mixture is centrifuged for 10 min at 13K, the alcohol is aspirated and the pellet is dried. 30 µl of water are added. The solution is centrifuged and frozen immediately at −80° C. The degradation and the amount are checked by placing 1 µl on a denaturing gel (1% agarose in TBE buffer (Tris, Base, EDTA), pH 8.5, autoclaved (BET 1 µg/ml).

B—Preparation of the messenger RNA bound to the membranes of the endoplasmic reticulum.

The cells are taken up in ice-cold hypotonic RSB buffer (10 mM KCl, 1.5 mM MgCl$_2$, 10 mM Tris-HCl, pH 7.4) treated beforehand with 0.1% DEPC at $10^8$ cells/ml. They are left on ice for 5 min. The cells are ruptured mechanically by means of 10 strokes of a DOUNCE homogenizer (type B). The homogenate is centrifuged at 1000 g for 2 min in order to sediment the nuclei. The supernatant or "cytoplasmic extract" is then used for the separation of free ribosomes/membrane extracts. 0.7 ml of cytoplasmic extract is mixed with 3.2 ml of 2.5M sucrose TK buffer (0.05M Tris-HCl, pH 7.4, 0.15M KCl, 0.005M MgCl$_2$), then this mixture is layered onto 2 ml of 2.5M sucrose TK. 8 ml of 2.05M sucrose TK are added, followed by 4 ml of 1.3M sucrose TK. The gradients are centrifuged at 4° C. for 5 h in a swinging rotor of the SPINCO SW28 type at 25000 rev/min. The tubes are punctured with a needle at the interphase between the 2.05M and the 1.3M sucrose gradients. One volume equal to TE 10:1 (10 mM Tris HCl, 1 mM EDTA) is added. An extraction is made with phenol, then with a phenol-chloroform mixture. Precipitation is effected with 1/10 of 3M NaAc and 2.5 vol. of ethanol.

For the isolation of the poly (A)$^+$ RNA a column of oligo (dT)-cellulose is used containing 1.2 ml of gel equilibrated with the loading buffer: 20 mM Tris-HCl (pH 7.6), 0.5M NaCl, 1 mM EDTA supplemented with SDS. The column is washed with $H_2O$, a 0.1M NaOH solution and 5 mM EDTA and water. It is then washed with 5 volumes of loading buffer. The RNA is dissolved in water and heated at 65° C. for 5 min. An identical volume of loading buffer is added twice. The temperature is allowed to equilibrate. The effluent is collected. It is heated at 65° C. and the sequence is repeated. The column is washed with 5 to 10 volumes of loading buffer, then with 4 volumes of loading buffer-0.1M NaCl. The poly(A)$^+$ is eluted with 2–3 volumes of 10 mM Tris-HCl (pH 7.5), 1 mM EDTA, 0.05% SDS.

3M sodium acetate (pH 5.2) is added at 1/10. Precipitation is effected with 2.2 vol. of ethanol.

II—Construction of the cDNA library

The in vitro preparation of the single-stranded complementary DNA starting from the messenger RNA bound to the membranes of the endoplasmic reticulum of the F55IIIE5 cell, followed by the double-stranded complementary DNA is carried out according to the techniques described by Gubler et al (6).

After protection of the internal EcoRI sites by the EcoRI methylase and size selection on an agarose gel at low temperature permitting the selection of fragments of size larger than 500 bp, the double-stranded cDNAs were cloned into the EcoRI site of the phage Lambda gt10 with the aid of the EcoRI linker.

The in vitro packaging of the recombinant Lambda gt10 phages was performed using a commercial cloning kit (Amersham Corp. Arlington Heights, Ill.).

After plating on E. coli C 600 Hfl$^+$, 6×10$^4$ recombinant phages are obtained.

III—Preparation of the complementary DNA probe

The preparation of the single-stranded complementary DNA probe is carried out by subtraction by means of two cycles of hybridization on an excess of messenger RNA of the cells said "to be eliminated" (Jurkat, Laz 388, U937, K562), followed by passage through hydroxyapatite columns which enables the double-stranded cDNA-mRNA complex to be separated. After 2 hybridization cycles and 2 passages through the column about 6–7% of the radioactivity remain, i.e. that about 7% of the F55IIIE5 material called MB ("membrane-bound") does not exist in the Jurkat, K562, U937 and Laz 388 cells. It is this material which serves as probe for the detection of the corresponding cDNAs in the MB-F55IIIE5 library. This technique makes use of the subtraction-hybridization conditions described by Davis et al (7).

Preparation of the subtracted probe/MB-FSSI-IIES-mRNA of Jurkat, K562, Laz 388, U937/

Starting from 5 µg of MB-F55IIIE5 mRNA, a single-stranded cDNA probe is prepared labelled with $^{32}$P-dCTP (specific activity : 800 Ci/mmol$^{-1}$) in a volume of 50 µl.

After incubation for 2 h at 42° C. with the reverse transcriptase enzyme, 5 µl of 0.2M EDTA are added, followed by 50 µl of 0.2N NaOH. The mixture is incubated at 65° C. for 1 h. 60 µl of 1N HCl and 30 µl of 2M Tris-HCl (pH 8) are added. 1/10th vol. of 3M NaAc is added. 7 µl of mRNA of each of the 4 tumor lines are added in order to precipitate the probe, then 2.5 vol. of ethanol are added.

The mixture is left for 1 h at −20° C. before being centrifuged, washed with 70% ethanol and dried. The precipitate is taken up in 7.5 µl of $H_2O$, and 7.5 µl of 0.5M $NaH_2PO_4$, pH 7, 1 mM EDTA, 0.25% SDS are added. The solution is incubated in the incubator at 68° C. for 20 hours.

The solution is diluted with 1 ml of 0.12M $NaH_2PO_4$, 0.1% SDS. It is loaded onto a hydroxyapatite column equilibrated with the same buffer at 60° C. The effluent (single-stranded material) is concentrated using Z-butanol and passed through a G-50 column in order to remove the phosphate buffer. 7 µg of mRNA of each of the lines are added again and the hybridization and passage through the column are repeated. After these 2 passages, 7% of the starting amount of radioactivity are recovered.

IV—Isolation and characterization of the cDNA clones

The previously constructed cDNA library (2×10$^4$ recombinant phages) is inoculated into E. coli C600/Hfl. The screening is performed in accordance with the usual techniques using nylon filters as described by Huynh (8).

Hybridization with the probe previously obtained is carried out at 42° C. with prehybridization with a hybridization solution of the Southern type and addition of 5×10$^6$ cpm/ml of the single-stranded MB-F55IIIE5 subtracted probe.

After two subtraction-hybridization cycles, 120 positive lambda gt10 phages are identified out of the 2×10$^4$ recombinants.

The plating of the positive phages, the purification of the corresponding DNAs, the purification of the complementary DNAs in the form of fragments by excision from an agarose electrophoresis gel with a low gelling point were carried out according to the method described by Maniatis (2) and Huynh (8).

The ligation of the longest cDNAs in the plasmid vector pBS digested by the EcoRI endonuclease and treated with the alkaline phosphatase calf intestine, the transformation of competent JM 109 bacteria and the screening of the recombinants by a double selection system (ampicillin+X-gal/IPTG) were carried out according to the methods of genetic engineering conventionally used.

The purification and the preparation on a large scale of the recombinant complementary DNAs cloned in pBS were carried out by using the method of purification on a cesium chloride gradient described by Maniatis (2).

A cDNA clone was isolated which has been designated FD47 and which consists of 400 bp and hybridizes with the probe obtained by subtraction-hybridization. This clone was selected, on the one hand, because it hybridizes with a transcript of 2 kb constantly found in the F55IIIE5 cells but not in the Jurkat, Laz 388, K 562 and U 937 cells in the "Northern blot" techniques and, on the other, because it shows no homology with any of the known sequences of the data bank entitled "Genebank". The FD47 clone contains a nucleotide region capable of coding for a hydrophobic transmembrane region.

V—Isolation and structure of a full-length DNA.

Among the 120 positive lambda g10 phages obtained after subtraction-hybridization, no other phage was observed to cross-hybridize with FD47.

In order to establish the sequence of cDNA called FDC, three new cDNA libraries are constructed starting either from oligo-dT primers, or a hexamer of random sequence or a specific primer consisting of the nucleotides 704 to 688 of FDC. Furthermore, a single-stranded RNA probe labelled with $^{32}$p is constructed starting from FD47 by in vitro transcription from the pBS plasmid using the T7 polymerase in the presence of $^{32}$P-UTP (800 Ci.mmole$^{-1}$) according to the method described by Triebel (5). The three libraries are constructed from the messenger RNA derived from CD3$^+$ clones bearing the γ and δ of the T receptor and which transcribe a LAG-3 message in considerable quantities when their RNA is tested with the FD47 probe.

The FD47 probe is used to screen the first cDNA library in order to obtain the clone FD19.

In the same manner as previously described, a 0.3 kb Bam HI–Hind III genomic fragment comprising the most 5' part of the IV exon is labelled using as primer a random hexamer and it is used to screen the second library to obtain the clones FD61 and FD101, and the third library in order to obtain a cDNA containing the almost full-length 5' end, called FD191.

The sequences of the clones FD47 and FD19 were determined directly in the pBS vector by the method of Sanger (9) using a universal M13 primer or a reverse M13 primer and the modified T7 polymerase.

The sequences of FD61, FD101 and FD191 were determined from single-stranded DNA after cloning in the vector M13mp18.

After different overlapping cycles of hybridization ("DNA walking") by using the 3 cDNA libraries obtained using different primers, cDNA clones are thus isolated, the sequences of which overlap and which cover a total of 1.8 kb.

The set of the total nucleotide sequences of these cDNAs called "FDC sequence" consisting of 1871 bp indicates that the messenger RNA of the LAG-3 gene has a long and open reading frame and codes for a protein of 498 amino acids, the peptide sequence of which is obtained by deduction from the nucleotide sequence of the cDNA.

The FDC cDNA itself was obtained by ligation of the 2 complementary EcoRI-HindIII fragments, one covering the 5' part of the FD191 clone, the other covering the 3' part of the FD19 clone, thus producing a clone covering the entire known sequence, as illustrated in FIG. 1.

VI—Isolation and structure of the LAG-3 gene

A/ Molecular cloning of the LAG-3 gene

Genomic DNA clones are isolated from the LY67 library made from DNA of a human B cell line transformed by EBV, partially digested with Mbo-I and inserted into the phage lambda 2001 as described by Dariavach (10). The FD47 insertion segment is labelled by means of the hexamer random priming method described by Feinberg (11) and used to screen $2 \times 10^5$ plaques of the human genomic DNA library. Nine positive plaques (GD1 to GD9) are isolated and the phage DNAs are characterized by restriction mapping using the FD19 probe containing half of the region coding for the protein and the untranslated 3' region.

Figures 2, 3:
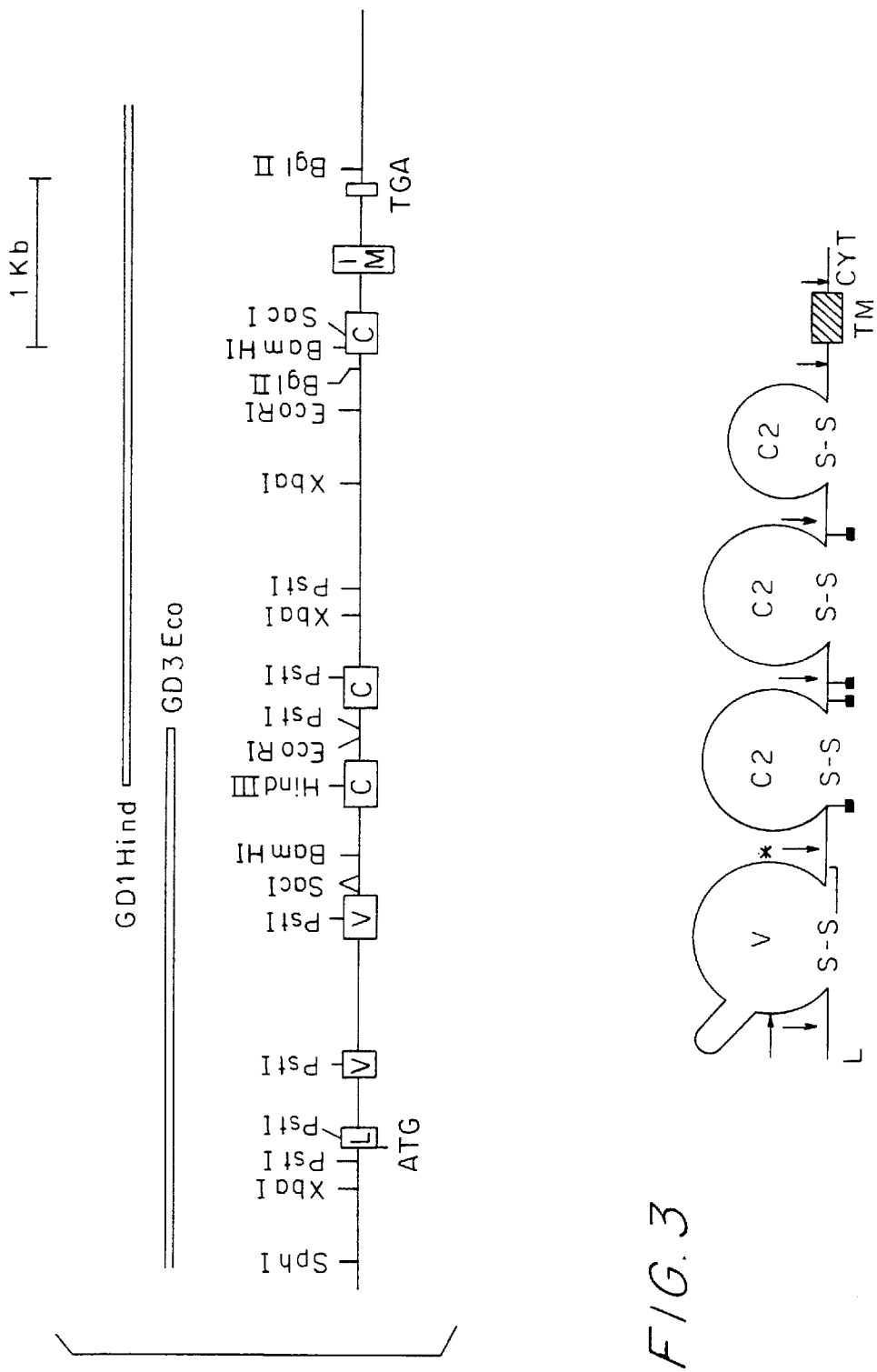
FIG. 2 presents the restriction map and the distribution of exons and introns in the LAG-3 gene.
FIG. 3 is a schematic representation of the LAG-3 protein.

Two overlapping DNA fragments of 16.4 kb (EcoRI) and 11.5 kb (Hind III) are obtained and subcloned in the plasmid pUN121 to give the clones GD3Eco and GD1Hind, as shown in FIG. 2.

Detailed restriction maps of these subclones are constructed and compared with the restriction map of the FDC sequence shown in FIG. 1.

Many fragments are obtained on an agarose gel with a low gelling point and are subcloned in the bacteriophages M13mp18 or M13mp19.

The sequences of these fragments are determined from single-stranded DNA using the dideoxy chain termination procedure described. Oligonucleotides containing 17 bases, the sequences of which are obtained either from the cDNA of FD19 or from the sequence of the 5' flanking region of the LAG-3 gene are synthesized and used for sequencing.

B—Structure of the LAG-3 gene

FIG. 2 illustrates the exon-intron organisation of the human LAG-3 gene. The map was constructed after single and double digestion by endonucleases of the $GD_2$ and $GD_3$ clones obtained from lambda 2001 and their subclones $GD_3$ Eco and $GD_1$ Hind. The untranslated regions are represented by a fine line.

The LAG-3 gene spans approximately 6.6 kb and is divided into 8 exons, the first nucleotides of which are located at positions 1, 289, 437, 742, 1012, 1288, 1531 and 1662 of the DNA sequence previously described.

The so-called promoter region at the 5' end of the LAG-3 gene whose sequence was previously described has been studied and enabled the following observations to be made:

no characteristic TATA box is found upstream from the 239-bp untranslated 5' region;

the nucleotide sequence contains a CCAAT box in reverse (i.e. ATTGG) at position −662 from the ATG sequence signalling the initiation of translation.

The CCAAT box is known to be crucial in many promoters and may function in the reverse orientation.

an Sp1 binding site containing the typical GGGCGG core hexanucleotide is also located at position −389 from the translation initiation site.

In order to estimate the number of copies of the LAG-3 gene in the human genome, the DNA of the K562 tumor cell line and of the polyclonal IL-2-dependent T and NK cell lines are digested with EcoRI, Hind III, Bam HI or XbaI. Southern Blot hybridizations are performed using the FDC probe (1871 bp), constructed by fusion of the 5' EcoRI/Hind III fragment of the FD191 clone with the 3' Hind III/EcoRI fragment of the FD19 clone. 3 fragments of 2, 8.2 and 10 kb are obtained with EcoRI, 2 fragments of 5.7 and 9.5 kb with Hind III, 3 fragments of 2.8, 4 and 13 kb with Bam HI and 3 fragments of 3, 4 and 6 kb with XbaI.

These results indicate that a single copy of the LAG-3 gene is present in the human haploid genome. Furthermore, the analysis of the T, B and NK cells using the same technique shows that there is no rearrangement of the LAG-3 gene in the cells during the differentiation of the lymphocytes.

VII—Expression of the LAG-3 gene

The 1004 bp fragment inserted in the FD19 clone was used as probe to analyse the cellular distribution of the expression and the regulation of the expression of the LAG-3 gene.

The results of the RNA "blotting" clearly show that the subtraction-hybridization procedures used in the first screening of the F55IIIE5 sub-library were performed successfully with respect to the isolation of the FD19 clone of the cDNA library in the sense that no LAG-3 transcript is expressed in the transformed cell lines of T, B and myeloid origin (in particular Jurkat, Laz 388, K 562, U 937).

Assays were performed on other lines of transformed T cells including CEM and MOLT-4 and none was found to express LAG-3. The same was true for the peripheral circulating monocytes.

A selection of polyclonal lines or clones of normal T and NK cells placed in culture was also tested. In the latter case, LAG-3 messenger RNA was detected as a single species of about 2 kb in all of the lines studied: 3 $CD3^-$ lines (F55 III E5, SIIH4, SIII G5), 4 $CD3^+$ TCR /$\beta^+$ lines ($CD4^+$: SIF8 and F55IIIG5 and one $CD3^+$ TCRτ/$\delta^+$ line (the clone $TCR\delta1^+$ TiτA$^+$ BK).

However, messenger RNA was not detected in fresh, purified T cells nor in peripheral macrophages nor in resting lymphocytes, within the limits of detection usually accepted for this technique.

The expression of the LAG-3 gene has also been studied in the nervous tissues of neuroectodermal origin and no messenger RNA was detected in either the neuroblastoma cell lines in culture or in fresh cerebral tissue.

The LAG-3 gene is only expressed in the T and NK cells after activation.

The expression of the LAG-3 gene is maximal 3 to 4 days after activation of the blood lymphocytes by phytohemagglutinin. Hence, the protein corresponds to what is appropriately called an activation antigen.

VIII—Structure of the LAG-3 protein

Figure 4:
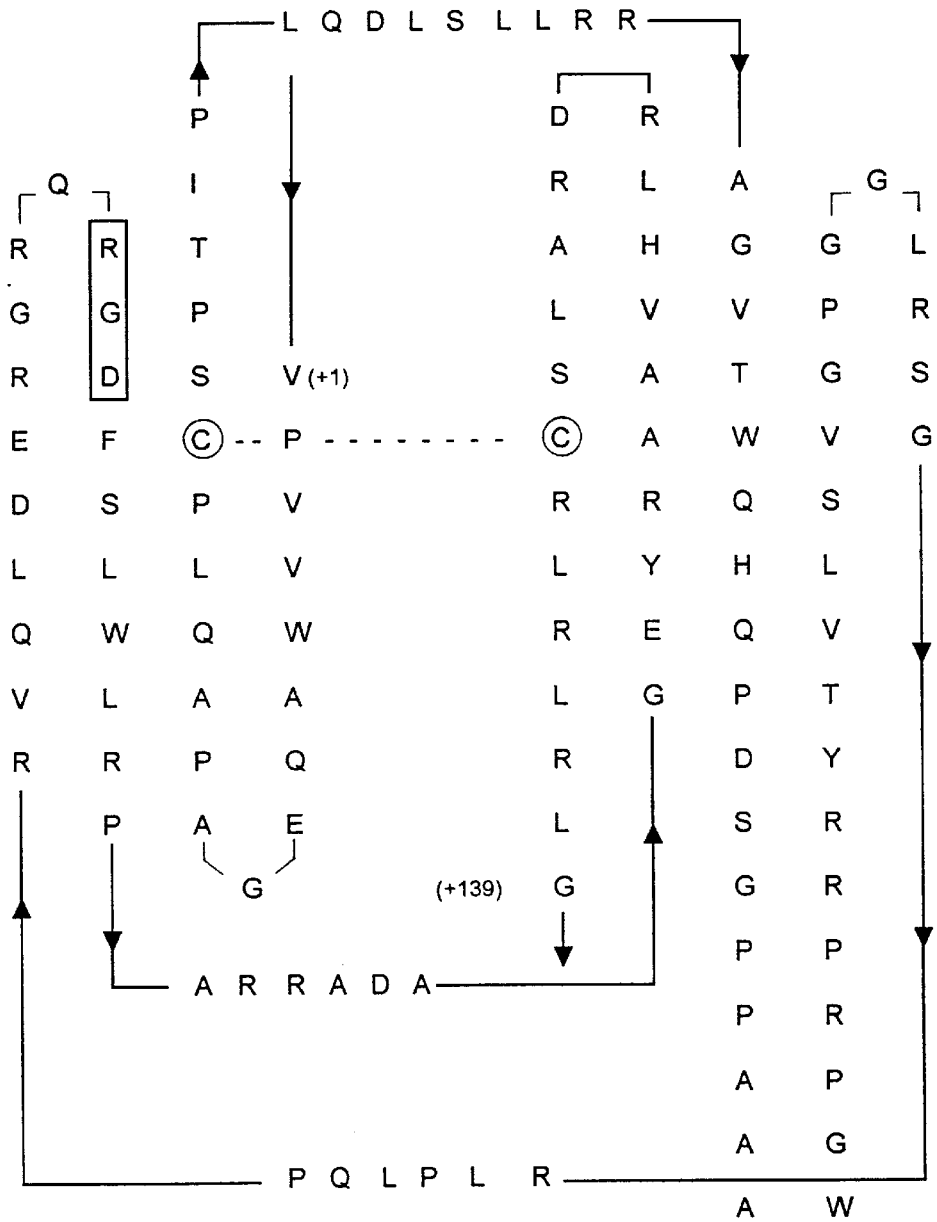
FIG. 4 presents a model of the domain 1 of the LAG-3 protein corresponding to amino acid residues 1 to 139 of SEQ ID NO:7.

The characteristics of the LAG-3 protein, shown in FIGS. 3, 4 and 6, have been deduced from the structure of the gene and from the analysis of its translation product. It appears to be a type I membrane protein containing 498 amino acids.

As shown in FIG. 3, the domains are designated by L (leader domain), V (V domain of the immunoglobulin type), $C_2$ ($C_2$ domain of the immunoglobulin type) (19), TM (transmembrane) and CYT (cytoplasmic). The position of the introns is indicated by arrows. The N-glycosylation sites(□) and the RGD(*) sequence (cell attachment sites) are also indicated.

The mature protein comprises 470 amino acids with a theoretical molecular mass of 51295 daltons and an isoelectric point of 10.9 based on protein structure analysis. It contains a leader peptide L (28 amino acids) encoded by the exons I (19 amino acids) and II (9 amino acids out of 50). The extracellular region is encoded by the exons II (41 amino acids out of 50), III (101 amino acids), IV (90 amino acids), V (92 amino acids) and VI (81 amino acids), the transmembrane (TM) region by the exon VII (44 amino acids) and the cytoplasmic region including strongly charged amino acids by the exon VIII (21 amino acids). The extracellular region contains 8 cysteine residues and 4 potential N-glycosylation sites (Asn-X-Ser, Thr).

FIG. 4 presents a model of domain 1 of the LAG-3 protein. The sequence of the first domain of the Ig type (amino acids+1 to +139) is represented according to the model used by Amzel and Poljak (12). The disulfide bridge is shown and the RGD sequence is boxed in.

The peptide segment encoded by the exons II and III corresponds to a V type IgSF domain as described by Williams (13) including the β-strands A, B, C, C', C", D, E, F and G shown in FIG. 6, possessing two unusual features.

Firstly, this V-type domain includes an extra loop of approximately 30 amino acids encoded by the first part of the exon III. This loop shown in FIG. 4 joins the β-strand C to the β-strand C' and contains, in particular, ten proline residues. It seems that such an insertion might be compatible with a IgSF-type fold to the extent that it does not cause rupture of the central core of the fold that is considered to consist of the β-strands A, B, E and G, F, C as described by Lesk (14).

This extra loop acts as immunogen since it is probably exposed at the outside of the molecule and consequently is exposed to recognition by antibodies.

As a general rule the differences in the V-type and C-type domains appear in the middle of the Ig-type fold at this site, i.e. in the region of the C β-strand.

Furthermore, the insertion of a peptide structure encoded by a supplementary exon (15), forming an additional miniloop, has been described in domain 4 of the N-CAM molecule.

The second unusual feature is that the cysteine downstream from domain 1 seems to be located in the β-strand G rather than in the β-strand F (residue 121), as is almost invariably the case. The sequence Asp-Gly-Tyr-Cys (SEQ ID NO:10) is located very characteristically in the β-strand F and is found here, except that an Ala residue replaces the Cys residue (FIG. 4). It seems possible that a disulfide bridge may be formed and, for example, it should be noted that an unusual disulfide bridge of a different kind has been oberved in the V-type domain of the chain of CD8 as described by Kirszbaum (16).

An Arg-Gly-Asp (RGD) sequence is found in the β-strand E (FIG. 4). This sequence is known to represent a potential adhesiotope as described by Ruoslahti (17) but it has not been established whether it forms the core of an essential binding site since, in this position, such a sequence would probably be located within the IgSF-type fold.

The exons IV, V and VI code for IgSF-related domains as described by Williams (13) with 51, 50 and 42 amino acids, respectively, between the two conserved cysteine residues. These three domains possess C-type folds and show sequence patterns characteristic of the C2-type domain (13). They have been compared with sequences of the C2-type domain with the aid of the ALIGN program according to the method described by Dayhoff (18) and Williams (19). Of 57 sequences examined, scores greater than 3SD (standard deviations) were obtained 32, 41 and 11 times for domains 2, 3 and 4, respectively. Domain 4 belongs to the truncated C2-type domain in the sense that it does not possess the β-strand D.

The domains 1 and 2 of LAG-3 were aligned and compared by eye with the domains 3 and 4, taking into account identities and structural considerations.

FIG. 5 shows the internal homology of LAG-3.

The amino acid sequences of domain 1 (starting from position 91 in FIG. 5 (and in accordance with the numbering in FIG. 5) after the extra loop) and domain 2 were aligned with the corresponding positions in domains 3 and 4. The identities are indicated by (*) and the similarities by (.).

Since domain 1 contains a sequence forming an extra loop, the alignment was begun at amino acid 91 in this domain and at amino acid 276 in domain 3 of FIG. 5. Out of 129 possible matches between residues, 34 identities, 35 similarities and 9 breaks were observed (alignment score greater than +8.5 SD). Moreover, in the β-strand F of domains 2 and 4, there is a W×C sequence which is most unusual at this position where the sequence Y or F×C is usually found, as described by Williams (13). Taken together, these results suggest that LAG-3 has evolved by gene duplication from a pre-existing two-domain structure resembling that of an Ig L chain.

The sequences of LAG-3 and CD4 of the rat have also been aligned, as is shown in FIG. 6. The dotted lines above the sequences show the positions of the β-strands in the four IgSF-type domains. The leader sequence L and the transmembrane sequence (TM) are shown by a continuous line above the sequence. The position of the introns is shown by arrows above the sequence (for LAG-3) and below the sequence (for CD4) as described by Maddon (20) for human CD4. Two large gaps are inserted corresponding to the sequence of the extra loop in domain 1 of LAG-3 and in order to account for the fact that domain 3 of CD4 is a V-type domain, whereas domain V of LAG-3 is a C2-type domain. The fragments of similarity comprise the start of domain 1 (9 identities and 10 similarities out of 17 possible matches), and the very unusual sequence W×C in domains 2 and 4 of LAG-3, which are also present at the corresponding positions in CD4. This sequence pattern is not found in an equivalent position in any other IgSF-type domain. Overall, there are 87 identities and 82 similarities out of 338 aligned residues (19 sequence breaks) when the extra-cellular regions of LAG-3 and CD4 of the rat are compared. One of the principal features of LAG-3 is, consequently, its relationship to CD4.

As in the LAG-3 structure known fragments having internal sequence homologies have been found in the CD4 molecule between domains 1 and 3 as well as between domains 2 and 4. More generally, the exon/intron organisation of LAG-3 and CD4 is very similar: both genes comprise an intron within the first IgSF-type domain and the position of the introns (shown by arrows in FIG. 6) in LAG-3 is very similar to that of CD4.

It has been suggested that CD4 has evolved by gene duplication from a pre-existing structure with 2 IoSF-type domains. The present discovery strengthens this hypothesis and the inventors suggest, on the basis of similarities of sequence and exon/intron organisation, that CD4 and LAG-3 have thus shared a common 4-domain ancestor.

The LAG-3 protein may thus be expected to function as do many other molecules of the superfamily of the Ig type as ligand for a soluble protein or for a membrane protein. The known examples include proteins whose expression is positively regulated by cell activation such as ICAM-1, known to be involved in cell-cell interactions, or ILL-R and IL6-R which function as receptors for growth factors.

In view of the fact that the LAG-3 protein is expressed in substantial amounts on activated lymphocytes (probably more than 5000 sites per cell given the limits of detection of indirect techniques of immunofluorescence with a rabbit anti-serum in flow cytometry) and taking into account its homology with CD4, the very likely function of LAG-3 is one of intercellular adhesion. The characterization of the receptor-ligand couples (for example ICAM-1/LFA-1 or CD4/MHC, class II) in this domain is in progress. The CD4 molecule has been crystallized and its atomic structure deduced by X-ray analysis (Ryu (22) Wang (23)). The binding sites for anti-CD4 antibodies, binding sites for the gp120 protein of HIV (AIDS virus) and the binding sites for molecules of class II of the major histocompatibility complex (MHC) have been studied and it has become clear that the first $NH_2$-terminal domain (domain 1) is the most important for the functional activity of CD4. It has been shown that soluble CD4 molecules obtained by deletion of the transmembrane and cytoplasmic parts of the natural CD4 molecule either alone or coupled to constant regions of immunoglobulins (creation of a CD4 immunoadhesin (Byrn 24)) are capable of binding the gp120 protein and of preventing the dissemination of infection by HIV. Similarly, with respect to the ICAM-1 molecule, it has been shown that the first $NH_2$-terminal domain (domain 1) contains binding sites for LFA-1 and attachment sites for the rhinoviruses (Staunton (25)). Two therapeutic applications which follow from knowledge of the structure of ICAM-1 have been described. The expression of ICAM-1 is considerably enhanced at the surface of the bronchial epithelium during asthmatic disease and in a model of a cynomolgus monkey made asthmatic, it is possible to reduce the infiltration of the bronchi by eosinophil granulocytes and to improve the clinical state by intravenous injection of anti-ICAM antibodies (Wegner (26)). In respect to the utilization of a recombinant molecule made soluble by deletion of the transmembrane and cytoplasmic domains, it has been shown that the soluble ICAM-1 molecule inhibits the infection of human cells by rhinoviruses by blocking the attachment of the virus to the natural ICAM-1 molecule at the surface of the cells by competition (Marlin (27)).

In view of the structural analogies with CD4, it is thus possible that LAG-3 may be a site of entry for a virus. As regards the HIV or related viruses, one of the possible attachment sites may consist (by analogy with CD4) in this case of all or part of the following amino acid sequence including, in particular, the β-strand C" of domain V: Gly Leu Arg Ser Gly Arg Leu Pro Leu Gln Pro Arg Val Gln Leu Asp Glu Arg (corresponding to the amino acids 80 to 97 of the LAG-3 protein, SEQ ID NO.7). Moreover, the LAG-3 gene has been localized on chromosome 12 (band p 13.3) (Triebel (28)) close to CD4. The study of human-hamster hybrid cells has shown that cell proteins encoded in genes of the human chromosome 12 (genes different from CD4) were necessary and sufficient for the expression of the HIV genes (Hart (29)). The LAG-3 protein might thus be involved in the reproductive cycle of the HIV, resulting in the production of infectious virions, independently of its possible capacity to act as receptor for the HIV.

Finally, structural homologies exist between the cytoplasmic region of the LAG-3 protein (in particular in the region of the peptide Arg Arg Gln Trp Arg Pro Arg Arg Phe Ser corresponding to amino acid residues 447 to 456 of SEQ ID NO:7) and various proteins encoded in the HIV genome, such as for example the REV protein (Yourno (30)) or FIV (Ratner (31)). These homology relationships suggest there again that the LAG-3 protein expressed by activated lymphocytes might play a role in the phases of replication or in the production of infectious viral particles of the HIV.

IX—Detection of the natural LAG-3 molecule.

Anti-LAG-3 rabbit antibodies were obtained after repeated injections of a synthetic peptide coupled to KLH into rabbits. This peptide comprises 30 amino acids forming the sequence shown in the sequence SEQ ID NO.3 included in the extra loop of domain V of LAG-3.

Figure 7:
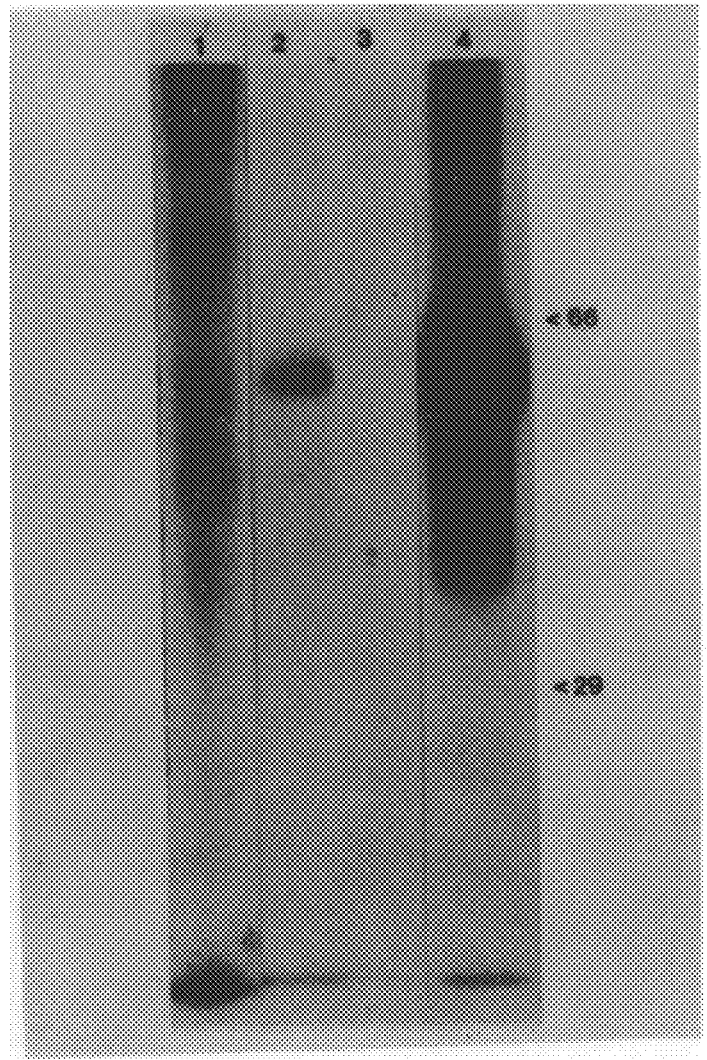
FIG. 7 presents the result of an immunoprecipitation of membrane proteins of PHA-blasts.

After labelling of the membrane proteins of T cells activated by phytohemagglutinin with $^{125}I$, immunoprecipitation by specific rabbit antibodies and purification on SDS-polyacrylamide gel, a single band of about 55 k daltons was detected under reducing and non-reducing conditions (FIG. 7). This observed molecular mass of about 55k daltons would correspond to the molecular mass derived from the analysis of the translation of the LAG-3 protein (51 k daltons) to which are added about 5 k daltons due to the presence of sugars (in particular at some of the 4 N-glycosylation sites), making the natural LAG-3 protein a membrane glycoprotein.

The LAG-3 protein does exist in the form of a single chain, probably glycosylated, at the surface of the T cells.

X—In vitro transcription and translation of the LAG-3 gene

In order to conclusively define the coding region and establish the capacity to be translated of the mRNA obtained by transcription of the FDC sequence, we have transcribed both strands of the FDC cDNA (Eco 47 III - Bgl II 209–1829 bp fragment) by using either the T3 or the T7 RNA polymerase using as substrate the FDC clone in the pBS vector. The two RNA preparations were then translated in vitro by using a rabbit reticulocyte extract in the presence of methionine 35S. The sense RNA containing the poly-A tail at the 3' end was translated into a protein of molecular mass of 55,000 daltons which could be detected by autoradiography after migration in a gel of the SDS-PAGE type. This estimated molecular mass is very similar to the theoretical molecular mass of 54457 corresponding to the 498 amino acids of the LAG-3 polypeptide with an intact, uncleaved signal peptide. No translation product larger than 20,000 daltons could be detected using the anti-sense LAG-3 RNA as substrate in the reaction with the rabbit reticulocyte extract.

XI—Expression of a transmembrane recombinant LAG-3 protein (LAG 3C) and a soluble recombinant LAG-3 protein (LAG 3-S).

We have employed a system using a vector of the "baculovirus" type. This system makes it possible to produce proteins of an insect (Spodoptera Frugiperda) foreign to the cells (SF9 cells) by using in vivo recombination between a transfer vector (plasmid p PVL 941) which contains the foreign gene, on the one hand, and the genome of a virus (Autographa Californica Nuclear Polyhedrosis virus AcMNPV), on the other. The viral genome is placed under the strong control of the promoter for the gene of the protein called polyhedrin. This system was described by Luckow (21) after transfection of the recombinant plasmid and the viral genome; the SF9 cells are selected by successive purifications (screening of recombinants), thus making possible the production of considerable amounts of recombinant protein. This protein is normally cleaved (the hydrophobic signal peptide is removed inside the cell) and glycosylated (at least partially).

1) Construction of the transfer vector a) Preparation of the vector

Figure 8:
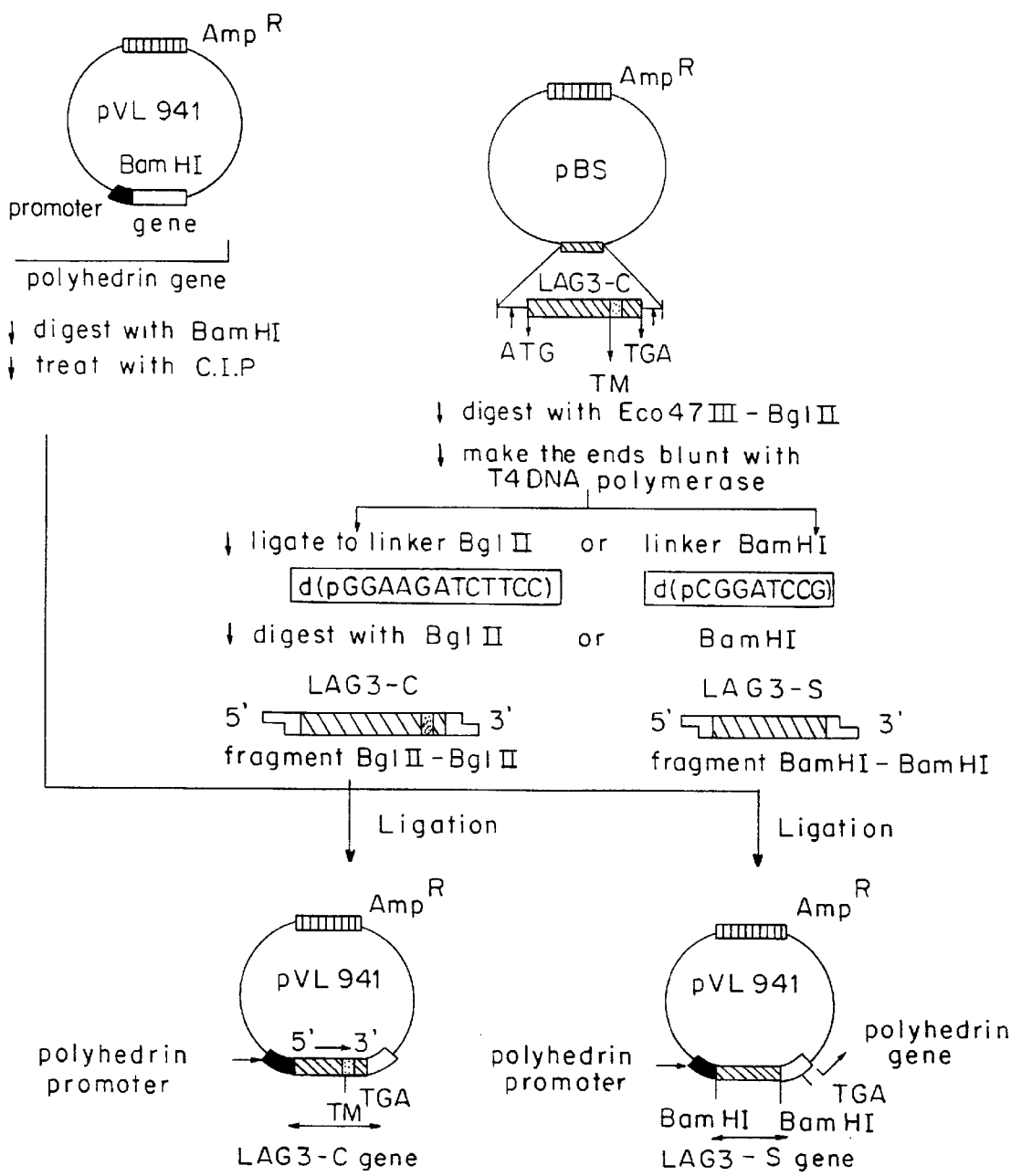
FIG. 8 is a schema for the preparation of a transfer vector (baculovirus system)

The schema for the preparation of the vector is shown in FIG. 8.

The vector PVL941 (obtainable from Dr. Max SUMMERS, University of Texas, U.S.A.) was cut by the restriction enzyme BamHI, then dephosphorylated by calf intestine phosphatase. This was done in order to prevent the autoligation of the vector with itself.

We then prepared from the FDC cDNA clone a fragment of 1620 base pairs resulting from digestion by the enzymes EC047 III (position 209 of FDC) and BglII (position 1829 of FDC). The ends cut, on the one hand, by the enzyme Eco47III and by the enzyme BglII on the other, were made blunt by a synthetic reaction with a Klenow DNA polymerase (T4 DNA polymerase). A double-stranded oligonucleotide (SEQ ID NO:11) "linker" containing a BglII restriction site was then attached to the Eco47III BglII FDC fragment in order to create the construction LAG 3-C (C for complete) and a linker containing a BamHI site was attached in order to create the construction LAG 3-S (S for soluble). After ligation, digestion was performed with an excess of restriction enzyme of the BglII type (in the case of the construction LAG 3-C) or of the BamHI type (in the case of the construction LAG 3-S), then the fragments corresponding to the 2 constructions were purified by gel electrophoresis. The last step consisted of linking the BglII LAG 3-C fragment or the BamHI LAG 3-S fragment to the vector PVL 941-BamHI.

b) Selection and amplification of the recombinant vectors

Competent JM109 bacteria were transformed with the recombinant transfer vector containing one or other of the constructions. Colonies resistant to ampicillin were placed in culture, then the plasmid DNA contained in these bacteria was purified; in this way, a number of clones containing the transfer vector was obtained and clones containing the LAG 3-C fragment or the LAG 3-S fragment in the right orientation were selected. In order to obtain the recombined plasmid in the pure state, capable of being used in transfection experiments, the clone of bacteria thus obtained was placed in culture in 500 ml of medium with ampicillin, then the plasmid was purified on a cesium chloride gradient.

c) Purification of genomic DNA of the virus

This was done according to the method described in "A manual of methods for Baculovirus vectors and insect cell culture procedures" provided by Dr. Max SUMMERS of the University of Texas, U.S.A.

d) Transfection of cells with the recombinant vector containing the LAG 3-C or LAG 3-S insert and the genome of the virus.

It concerns the co-transfection of SF9 cells with, on the one hand, the purified recombinant vector and the viral genome on the other using the calcium chloride method. This was done in accordance with the conditions described in the manual referred to in c).

e) Selection of the recombined viruses

5 Days after transfection, the supernatants of the SF9 cells were recovered, then assayed. These assays are performed by infecting fresh SF9 cells with successive dilutions of this primary culture supernatant. Initially, there are considered to be $10^7$ pfu/ml (pfu="plaque forming unit") and successive dilutions are made so as to obtain between 100 and 1 pfu/ml. After 3 days, the SF9 cells thus infected are assayed by the "dot blot" hybridization procedure. The cells are lysed with NaOH, transferred to nylon and hybridized with a probe corresponding to the FDC fragment of 1871 base pairs. After washing and autoradiography, the positive wells are located and the wells corresponding to the highest dilutions are retained. This screening technique is performed a second and third time. During the third screening, a check is made that the dots giving a positive signal in "dot blot" hybridization do not contain SF9 cells containing inclusions. These inclusions correspond to the secretion of the protein polyhedrin, produced after infection of SF9 cells by a non-recombined, wild-type virus. This last point was also checked not by direct reading of the plaque but by a procedure involving collection of the cells, spreading them on a glass slide and staining with May-Grünwald-Giemsa.

f) Detection of the recombinant protein LAG 3-C and LAG 3-S.

Figure 9:
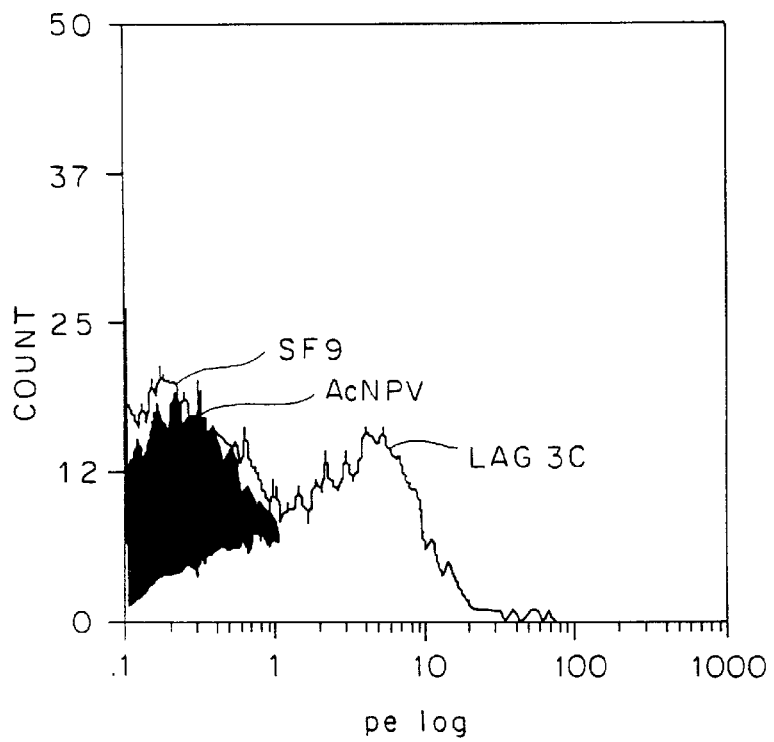
FIG. 9 presents the result of the detection by immunofluorescence of LAG-3C in the baculovirus system by means of a heteroantiserum.
Figure 10:
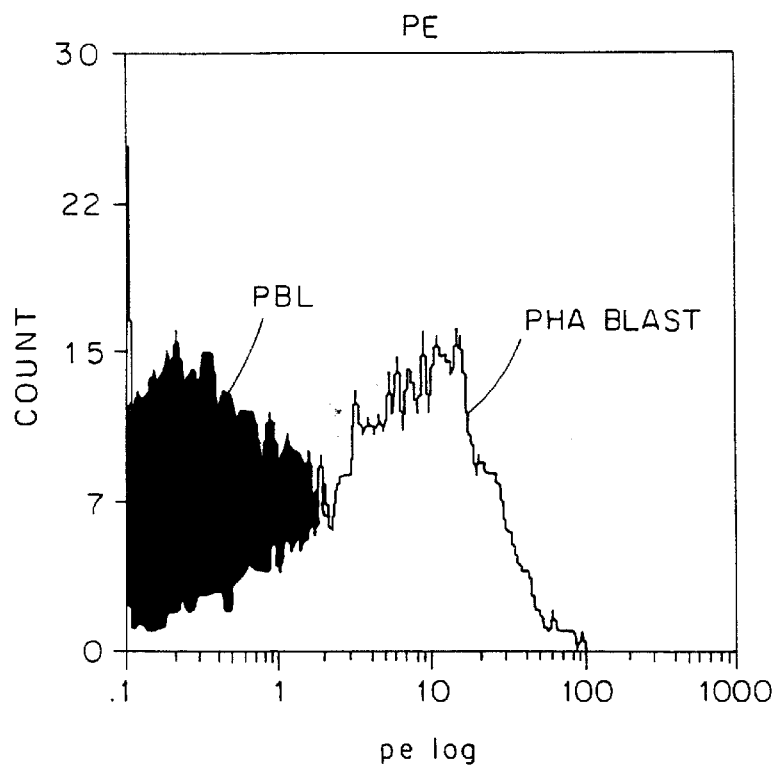
FIG. 10 shows by immunofluorescence the reactivity of a heteroantiserum on PHA-blasts and PBL.

SF9 cells infected with the recombinant viral clone containing the LAG 3-C fragment were obtained on the 5th day of culture after an infection at 0.1 pfu/cell. These SF9 cells express the recombinant LAG-3 molecule at the surface as is shown by the immunofluorescent reactivity of the specific rabbit antibody, compared with the reactivity obtained with uninfected SF9 cells or SF9 cells infected with a AcNPV wild-type virus (FIG. 9). Furthermore, the reactivity of the LAG-3-specific rabbit serum towards the SF9 cells expressing LAG-3 was compared with the reactivity obtained towards T lymphocytes activated by phytohemagglutinin (PHA-blasts). The histograms obtained are similar and thus show that the number of recombinant LAG-3 molecules (FIG. 9) expressed at the surface of the SF9 cells is comparable to the number of natural LAG-3 molecules expressed at the surface of the activated lymphocytes (FIG. 10).

Figure 11:
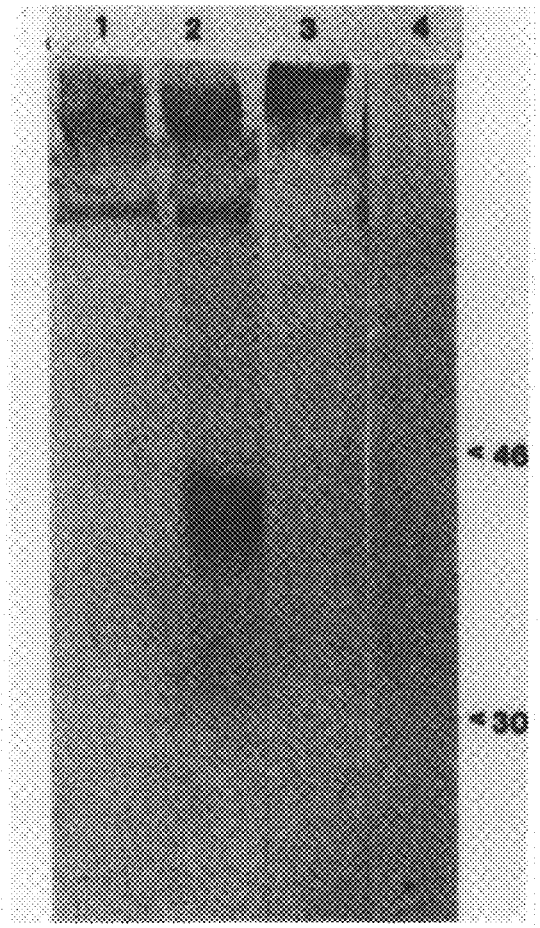
FIG. 11 presents the result of the detection of LAG-3S in the baculovirus system by means of a heteroantiserum in a Western blot.

Supernatants of SF9 cells infected with the recombinant viral clone containing the LAG 3-S fragment were obtained on the 5th day of culture after an infection at 0.1 pfu/cell. A supernatant was assayed by the so-called "Western blot" technique with the anti-loop antipeptide antibodies of domain V described in section IX. A pure signal corresponding to a protein of about 45 kd was obtained after revelation with anti-rabbit goat antibodies labelled with peroxidase (FIG. 11).

This molecular mass corresponds well with the mass expected of the LAG 3-S Eco47 III-BamHI fusion protein (38038K daltons) after glycosylation in the SF9 cells.

The structure of the part coding for LAG 3-S (SEQ ID No.5) shows that the first three domains of LAG-3 (upstream from the internal BamHI site) were fused with a nucleotide segment of 56 base pairs of the gene for polyhedrin downstream from the BamHI site. In total, after cleavage of the signal peptide of 28 amino acids, the fusion protein comprises 352 amino acids, 335 corresponding to LAG-3 and 17 being derived from one of the reading frames of the gene for polyhedrin.

XII—Production of anti LAG-3 monoclonal antibodies

The peptide of 30 amino acides having the sequence shown in the sequence SEQ ID No 3 was coupled at its $NH_2$ terminus to the tetanus antitoxin carrier protein. BALB/c mice were immunized by an initial intraperitoneal injection of 50 μg of tetanus toxoid coupled peptide in CFA, followed by injections on days 15,30 and 50 in IFA. On day 70, mice were boosted via intravenous injection of 20 μg of peptide in NaCl solution (0.9%), and 3 days later immunized splenocytes were fused with NS1 HAT-sensitive myeloma cells.

Hybridoma supernatants reactive on both LAG-3 surface-expressing Sf9 cells and PHA-activated T cells (PHA blasts) were selected by indirect immunofluorescence and subsequently subcloned in HAT medium supplemented with 10% FCS.

Two murine hybridoma supernatants, designated 17B4 (IgG1) and 4F4 (IgM) were selected upon their reactivity in immunofluorescence assays on AcLAG-3Cv (for A. California LAG-3C recombinant virus)-infected Sf9 cells and their lack of binding to either noninfected Sf9 cells or wild-type AcNPv-infected Sf9 cells.

Figure 12:
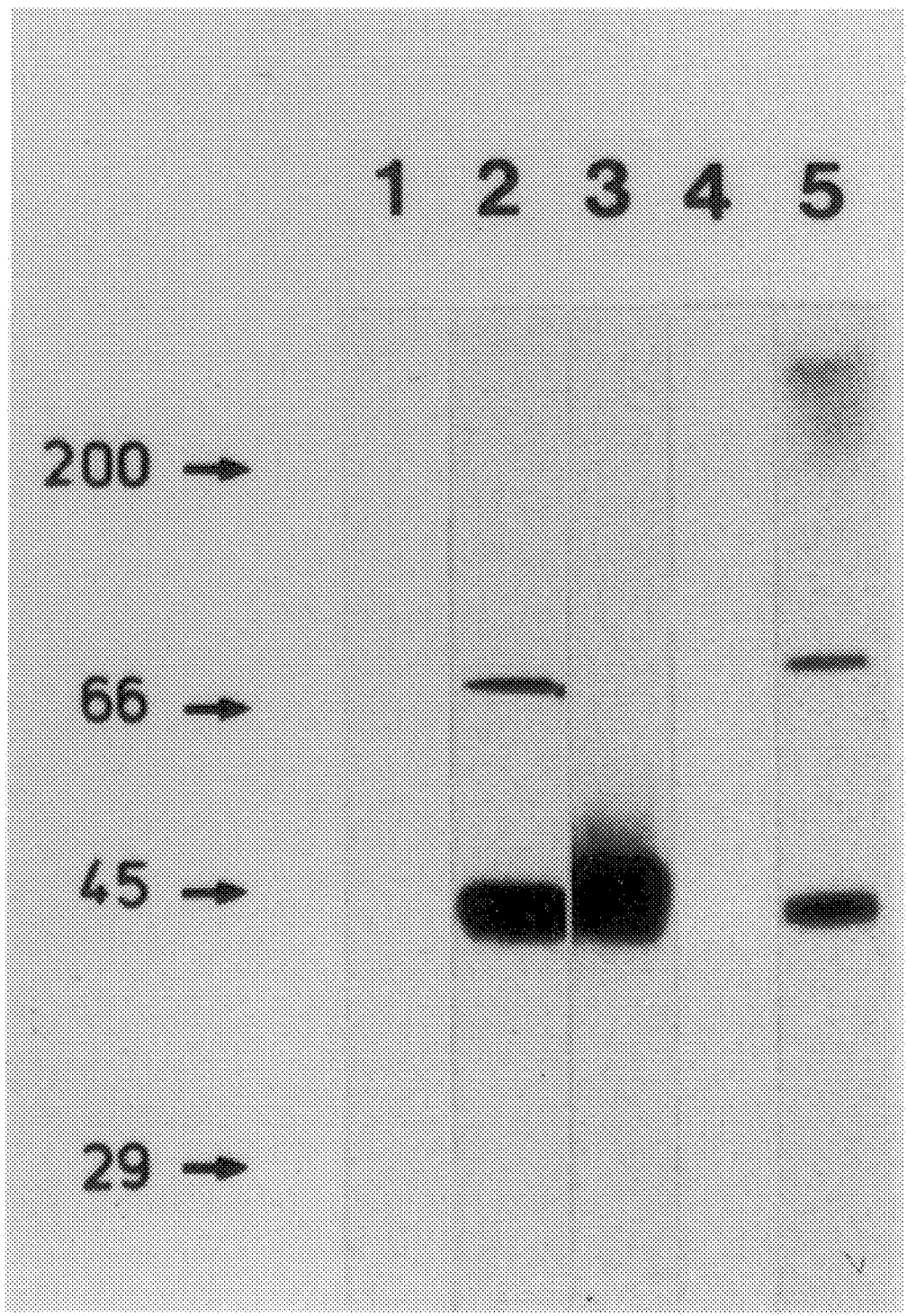
FIG. 12 shows the Western blot analysis of ACLAG-3Sv-infected SF9 cell supernatant at day 6 post-infection.

Monoclonal (17B4 and 4F4) anti-LAG-3 antibodies were tested for their ability to recognize a soluble recombinant LAG-3 protein (LAG-3S) corresponding to the three $NH_2$ terminus Ig-like LAG-3 domains by Western blot analysis of AcLAG-3Sv-infected Sf9 cell supernatant. FIG. 12 shows the Western blot analysis of ACLAG-3Sv-infected SF9 cell supernatant at day 6 post-infection. The nitrocellulose transfer membrane was incubated with anti-NKTa (lane 1), 4F4 (lane 2), 17B4 (lane 3), preimmune rabbit serum (lane 4) or polyclonal rabbit antiserum, obtained in part IX (lane 5). The anti LAG-3 antibodies recognized a 43-kD protein band. The translation of the 35r-aa recombinant LAG-3S protein should result in a 38-kD molecule; this size difference may derive from the addition of N-glycans by the Sf9 insect cells. Together, these data demonstrated that immunization with the peptide has allowed the generation of anti-LAG-3-specific reagents.

Initial experiments showed that both the 17B4 and 4F4 mAb reacted with PHA-activated PBMC. The fine specificity of 17B4 was assessed in competition experiments using the 30-aa peptide (sequence SEQ ID No 3) and a 28-aa LAG-3 unrelated peptide (termed NS). Preincubation of the 17B4 mAb with a 20-nM concentration of the peptide abrogated 17B4 binding to PHA blasts. Anti-LAG-3 mAb competitive binding to PHA blasts indicated that cell preincubation with saturating amounts of 17B4 abrogated 4F4 binding. Together, these dates confirmed that both antibodies recognize specifically the extra loop segment of the LAG-3 Ig-like first domain and showed that they are likely to react with the same or a closely related epitope provisionally termed LAG-3.1.

XIII—Cellular distribution of the LAG-3.1 epitope

Figure 16:
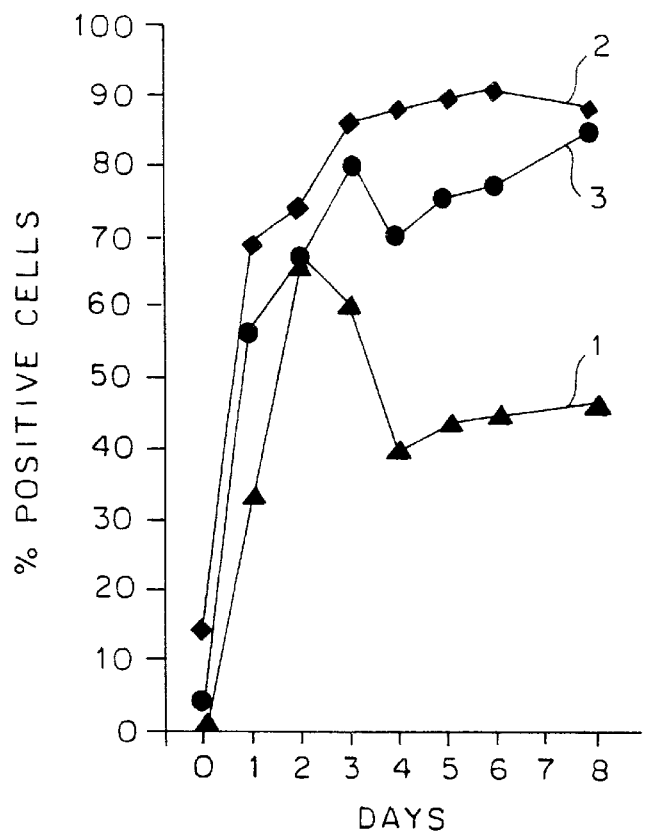
FIG. 16 shows the results of a study of the kinetics of LAG-3.1 epitope expression on PBMC by indirect immunofluorescence from day 0 to 8 after PHA activation.

The kinetics of LAG-3.1 epitope expression on PBMC was studied by indirect immunofluroescence from day 0 to 8 after PHA activation. Other activation antigens such as CD25 (IL-2R) and CD71 (transferrin receptor) were assessed in parallel. The results espressed as % of positive cells and shown on FIG. 16 are given with 17B4 (1), anti CD25 (2) and anti CD71 (3).

At day 0, PBMC do not express the LAG-3.1 epitope. 17B4 binding was not detected at 6 h, appeared at day 1, peaked at day 2 with >60% of the cells being positive, decreased progressively until day 8 and became virtually undetectable at day 11. Restimulation of PHA blasts at day 11 by addition of either IL-2 (25 and 250 U/ml), IL-4 (2.5 and 25 U/ml) or IFN-γ (10 and 1,000 U/ml) indicated that only IL-2 (at 250 U/ml) was able to reinduce the expression of the LAG-3.1 epitope.

A series of long-term cultured IL-2 dependent clonal or polyclonal T cells, including MBA8, T2, R2, PH28, 1C1 ($CD3^+TCR-\alpha/\beta^+$), TH6-4, BK($CD3^+TCR-\gamma/\delta^+$), as well as the NK cell lines F55IIIE5 and SIB5 ($CD3^-CD56^+$), were tested and all found to express (at varying density) the LAG-3.1 epitope. Conversely, a series of transformed cell lines did not express the LAG-3.1 epitope : T cells (PEER, HSB2, REX, CEM, JURKAT, MOLT-4), B cells (LAZ388, LAZ461, RAJI, RAMOS, DAUDI, E418), and nonlymphoid cells (K562, HL-60, U-937, KG-1).

Taking advantage of the 4F4 mAb IgM isotype, coexpression by day 2 PHA blasts of the LAG-3.1 epitope and other molecules (CD4, CD8, CD3, CD56, or CD25) was studied by double-color immunofluorescence analysis. The LAG-3.1 epitope was expressed on a majority of $CD3^+$ (63% of them being LAG-3$^+$), $CD25^+$ (53%), $CD4^+$ (58%), or $CD8^+$ (60%) lymphocytes. Approximately 3% of the PHA blasts expressing LAG-3.1 were $CD3^-$. An equivalent fraction was $CD56^+$. It is therefore likely that the corresponding cells were activated $CD3^-CD56^+$ NK lymphocytes. Together, these results show that the LAG-3 molecule is present on a majority of activated T ($CD4^+$ or $CD8^+$) cells and on some NK cells at day 2 after PHA activation.

The LAG-3.1 epitope was not found on resting B cells nor on cultured (PWM-stimulated) peripheral blood B cells expressing the CD20 molecule; in these experiments the expression of CD71 (transferrin receptor) was used as a control for cell activation. The LAG-3.1 epitope was not found in tonsils where a large fraction of the B cells constitutively express CD71, in resting monocytes, or LPS-activated monocytes (D). Together, these results confirm that LAG-3 is selectively (i.e., T and NK cells as opposed to B cells and monocytes) expressed on a large fraction of activated PBMC.

XIV—Biochemical characterization of LAG-3 protein

The following methods were used

Immunoprecipitation of the antigens Cell surface labeling using $^{125}I$ was performed by a standard lactoperoxidase method (Moingeon et al. (32)), and immunoprecipitations were carried out as previously described by Ythier et al. (33). Briefly, cell pellets were resuspended in 1 ml of lysis buffer at pH 7.2 containing 10 mM sodium phosphate, 1% TRI-TON X-100, 0.15M NaCl, 1 mM EDTA, 1 mM EGTA, 1 mM Naf, 1 mM PMSF, 1 mg trypsin inhibitor, 1 mM iodoacetamide, and 0.1% sodium deoxycholate. Extensive preclearings were carried out and specific immunoprecipitations were performed sequentially with antiactin (an IgGl) anti-NKTa (an IgGl used as negative control), 17B4 (IgGl), and finally the XC3 anti-CD2 mAb. All the mAbs were coated to protein G-Sepharose beads and incubations with cells lysates were performed overnight at 4° C. After washing the beads in lysis buffer, samples were eluted by boiling in SDS sample buffer in the absence or in the presence of 5% 2-ME, and analyzed in 10% SDS-PAGE under nonreducing or reducing conditions. Gels were stained with coomasie blue, dried, and autoradiographed at 8° C.

N-deglycosylation treatment of glycoproteins

After autographic detection, the immunoprecipitated labeled proteins were excised, eluted, and lyophilized. The recovered material was rehydrated in 10 μl of 0.5% SDS buffer and denaturated by boiling for 4 min. Digestion with 0.2 U of N-glycosidase F (PN Gase-F; Boehringer, Mannheim, Germany) was carried out overnight at 37° C. in a 40 pl buffer (pH 7.5) containing 250 mM sodium phosphatase, 10 mM EDTA, 10 mM 2-ME, and 1% NOG (n-octyl β-D-glucopyranoside). Cleavage products were resuspended in an equal volume of SDS sample buffer containing 5% 2-ME and analyzed by SDS-PAGE.

Figure 13:
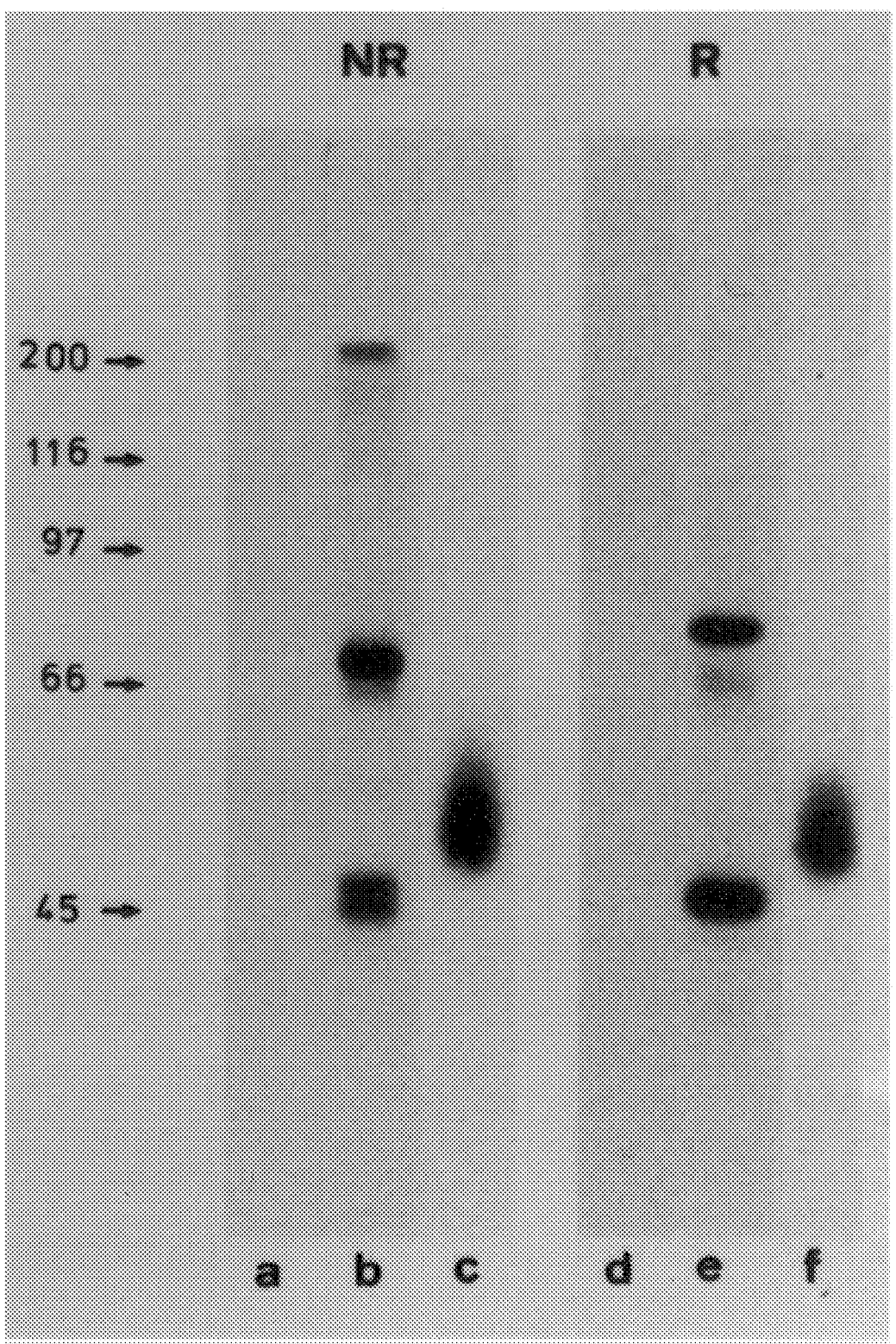
FIG. 13 shows the results obtained by SDS-PAGE analysis of immunoprecipitates from PHA blasts by using anti-NKTa (lanes a and d), 17B4 (lanes b and e), or anti-CD2 (lanes c and f) under non-reducing conditions (NR) and under reducing conditions (R)

On FIG. 13 are reported the results obtained by SDS-PAGE analysis of the immunoprecipitation from PHA blasts by using anti-NKTa (lanes a and d) 17B4 (lanes b and e) or anti-CD2 (lanes c and f) under non reducing conditions (NR) and under reducing conditions (R).

SDS-PAGE analysis of the 17B4 immunoprecipitates from PHA blasts (lane b) resolved in on reducing conditions a 42–45-kD doublet band in addition to the 70 kD LAG-3 molecule. Under reducing conditions, the doublet band appeared as a single 45 kD species (lane e). Extensive preclearing of the lysates with antiactin mAb-coupled beads could rule out a possible contamination with actin molecules. Immunoprecipitation positive and negative controls were performed by using anti-CD2 (lanes c and f) and anti-NKTa (lanes a and d) mAbs, respectively.

When PHA blasts lysates were boiled in the presence of 0.5% SDS, 2 mM DTT (or with SDS alone, data not shown) before immunoprecipitation with 17B4, only the 70 kD protein was detected in SDS-PAGE suggesting that the 70 kD protein but not the 45 kD proteins, is LAG-3 encoded.

Figure 14:
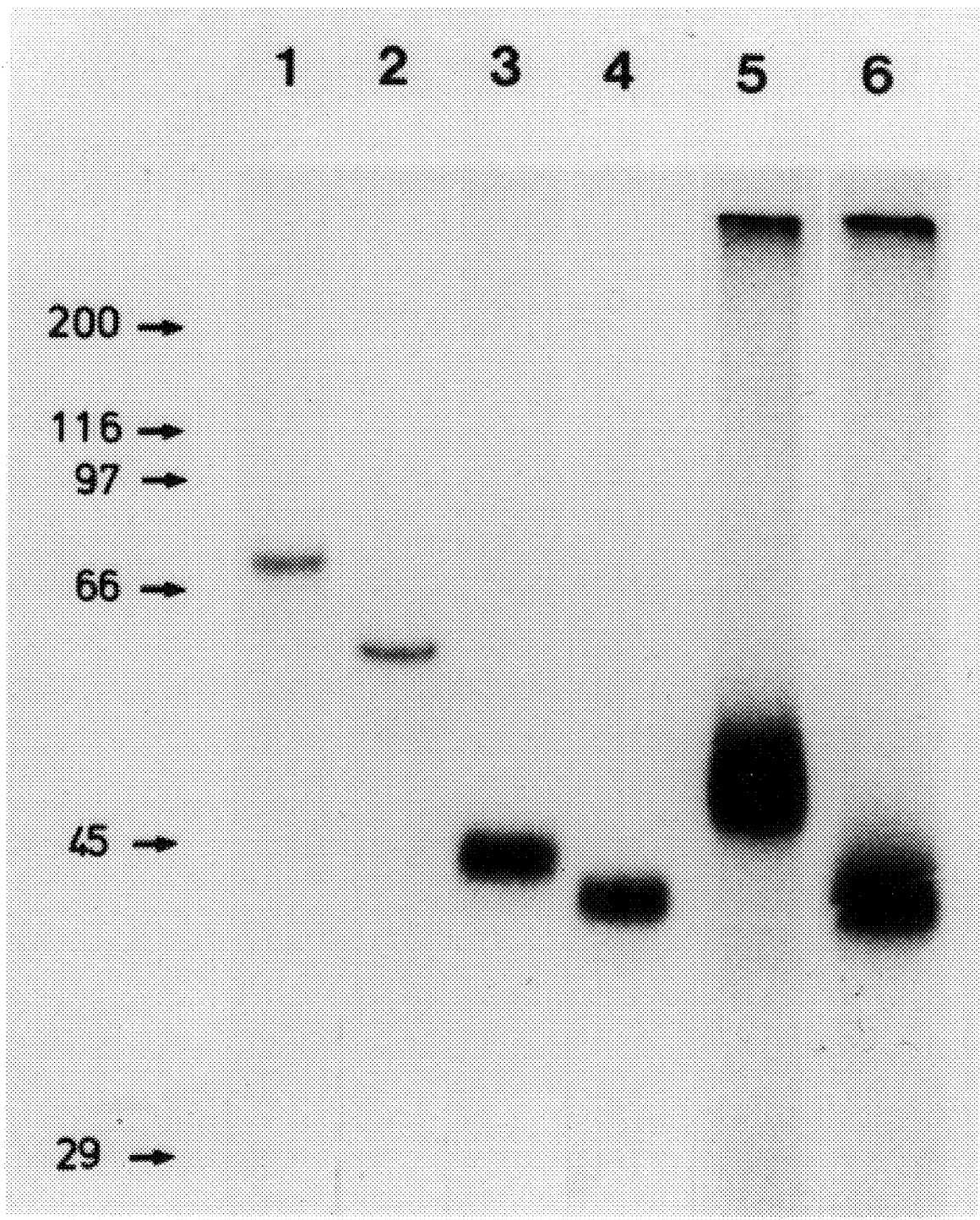
FIG. 14 shows the results of analysis by SDS-PAGE under reducing conditions of two proteins (70 and 45 kD) immunoprecipitated from PHA blasts that were extracted from the gel and independently submitted to N-glycosidase-F treatment.

Together, the results of the immunoprecipitation experiments performed on activated T and NK cell lysates indicate that LAG-3 is noncovalently associated to one 45 kD molecule. The two proteins (70 and 45 kD) immunoprecipitated from PHA blast lysates were extracted from the gel and independently submitted to N-glycosidase-F treatment. Samples were analyzed by SDS-PAGE under reducing conditions. The results are reported on FIG. 14.

Reduction in size was observed for both species from 70 to 60 kD (lanes 1 and 2) and from 45 to 40 kD (lanes 3 and 4), indicating that molecules are glycosylated. The difference seen between the apparent mass of LAG-3 (60 kD) after N-glycosidase-F treatment and the predicted molecular mass of the mature protein backbone (51 kD) may be related to incomplete N-deglycosylation (four potential N-linked glycosylation sites in the LAG-3 sequence) or to other posttranslational modifications.

XV—B Lymphocyte adhesion to LAG-3-transfected COS cells

The high-level expression cellular system based on COS-7 cell transfection with recombinant CDM8 vectors (Seed B. (34)) was used. This system has proved to be the most convenient to study binding of transiently expressed wild-type and mutant CD4 with low affinity to HLA class II and with high affinity to gp120. Transfections of COS-7 cells were performed in parallel with the CDM8-LAG-3 and CDM8-CD4 recombinant vectors. Cell surface expression, rosette formation with class II-bearing B lymphocytes, and gp120 binding were assayed. A LAG-3 insert clones in the reverse orientation, termed CDM8-GAL, was used as negative control.

As shown by flow cytometry analysis with 17B4, 30–40% COS-7 cells assessed on day 3 were found to express LAG-3 specifically. COS cells transfected with the reverse construction GAL were not reactive with 17B4. Adhesion of the HLA class II-expressing Burkitt lymphoma line, Raji, occurred only with LAG-3-expressing COS cell (23±3%, n=26), as detected by immunoperoxidase staining with the 17B4 antibody. Rosettes of Raji cells formed with LAG-3 and CD4-positive COS cells were morphologically indistinguishable.

These results suggested that rosette formation was induced by the interaction of HLA class II and LAG-3 molecules.

Figure 15:
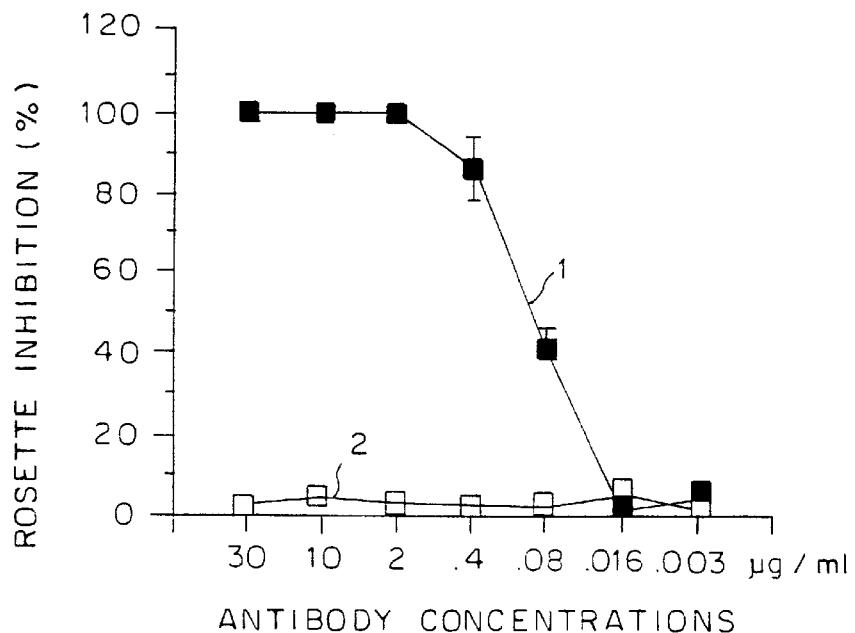
FIG. 15, graph 1 shows that rosettes between LAG-3-positive COS cells and Raji were specifically inhibited in a dose-dependent manner by the LAG-3-specific 17B4 mAb.

Rosettes between LAG-3-positive COS cells and Raji were specifically inhibited in a dose-dependent manner by the LAG-3-specific 17B4 mAb (FIG. 15, graph 1).

In contrast, no inhibition was observed with the isotype-matched (IgGl) anti-CD4 mAb, OKT4E (FIG. 15, graph 2), which is a potent inhibitor of rosettes between CD4-positive COS cells and Raji. These results demonstrate that cellular adhesion is directly dependent upon specific LAG-3/HLA class II interaction.

XVI—Production of anti-LAG-3 monoclonal antibody by using LAG-3 S.

One liter of supernatant of SF9 cells infected with the recombinant viral clone containing the LAG-3 S fragment (as disclosed in chapter XI) was purified on a S-Sepharose fast flow column by using a FPLC system (Pharmacia). The elution with NaCl 0.3M provided a "semi-purified" fraction containing about 1% of LAG-3 S proteins.

Biozzi mice were immunized by an initial intraperitoneal injection of 1 µg of the semi-purified fraction of LAG-3 S in incomplete Freund's adjuvant, followed by 3 intraperitoneal injections each on days 15, 30 and 45 of 1 µg of the semi-purified fraction in incomplete Freund's adjuvant and finally 3 days before the fusion by I.V. injection of 1 µg semi-purified fraction without adjuvant.

The obtained hybridoma were selected by testing their supernatant for their ability to label SF9 or COS cells expressing recombinant LAG-3 on the membrane.

One hybridoma supernatant was thus selected and named 15A9.

The monoclonal antibody 15A9 has a reactivity which is similar to the monoclonal antibody 17B4 on PHA blasts, SF9 or COS cells expressing LAG-3.

The isotype of 15A9 is IgG1. This antibody recognizes one of the three first domains of LAG-3. The reactivity of 15A9 with PHA blasts is not inhibited by a 1 µg/ml of the peptide having the sequence SEQ ID No 3:15A9 does not recognize this peptide and is thus different from 17B4.

XVII—Use of anti LAG-3 monoclonal antibodies

Anti LAG-3 monoclonal antibodies such as 17B4 and 15A9 may be used for detecting in vivo in humans the infection or inflammation sites where there are usually both activated T lymphocytes (expressing LAG-3) and cells of the inflamed tissue expressing HLA class II molecules.

Anti LAG-3 monoclonal antibodies may also be used as anti-inflammatory drugs for inhibiting the interactions between activated T lymphocytes and cells expressing Class II molecules in the site of inflammation. More generally these monoclonal antibodies may be used during chronic inflammatory diseases or auto-immune diseases such as lupus erythematosus, auto-immune thyroiditis, multiple sclerosis, some types of diabetes, rheumatoid arthritis, psoriasis and generally in the treatment of diseases which are presently treated with corticoids.

Deposits

Hybridoma producing 17B4:1–1240 at C.N.C.M.
Hybridoma producing 15A9:1–1239 at C.N.C.M.
The deposits were made on Jul. 10, 1992.

REFERENCES

1. Nowill, A. et al., J. Exp. Med. 163, 1601.
2. Maniatis, T. et al., 1982. Molecular cloning : A laboratory manual, Cold spring harbor laboratory New York.
3. Mechler, B. et al., J. Cell Biol. 88, 29 (1981).
4. Aviv et al., Proc. Natl. Acad. Sci. USA 69 : 1408.
5. Triebel, F. et al., Eur. J. Immunol. 17, 1209.
6. Gubler, U. et al., Gene. 25, 263.
7. Davis, M. M. et al., Proc. Natl. Acad. Sci. USA. 81:2194.
8. Huynh, T. V. et al., DNA cloning : A practical approach. 49–78, D. Glover Editor. IRL Press. Oxford. United Kingdom.

9. Sanger, F. et al., Proc. Natl. Acad. Sci. USA 75, 5463.
10. Dariavach, P. et al., Proc. Natl. Acad. Sci. USA. 84, 9074.
11. Feinberg, A. P. et al., Anal. Biochem. 132, 6.
12. Amzel, L. M. et al., Ann. Rev. Biochem 48, 961 (1979).
13. Williams, A. F. Immunol. Today 8, 298 (1987).
14. Lesk, A. M. & Chothia, C.J. Mol. Biol. 160, 325 (1982).
15. Santoni, M. J. et al. EMBO J. 8, 395 (1989).
16. Kirszbaum, L. et al., J. Immunol. 142, 3931 (1989).
17. Ruoslahti, E. et al., M.D. Cell 44, 517 (1986).
18. Dayhoff, M. O. et al., Enzymol. 91, 524 (1983).
19. Williams, A. F. et al., Ann. Rev. Immunol. 6, 381.
20. Maddon, P. J. et al. Proc. Natl. Acad. Sci. USA 84, 9155 (1987).
21. Luckow, V. A. et al., Bio/Technology, 6:47.
22. Ryu S. E. et al., Nature, 348, 419.
23. Wang J. et al., Nature, 348, 411
24. Byrn R. A. et al., Nature 344, 667
25. Staunton D. E. et al., Cell. 61, 243
26. Wegner C. D. et al., Science 247, 456
27. Marlin S. D. et al., Nature 344, 70
28. Triebel F. et al;, J. Exp. Med., 171, 1393
29. Hart E. C. et al., Science, 240, 488
30. Yourno J. et al., AIDS Res. Hum. Retroviruses 4:165–173 (1988).
31. Ratner L. et al., Nature, 313:277–284 (1985).
32. Moingeon P. et AL., Nature, 323, 638, 1986.
33. Ythier A. et al., Cell Immunol., 99, 150, 1986.
34. Seed B., Nature, 329, 840, 1987.

Symbols of the Amino Acids

A Ala alanine
C Cys Cysteine
D Asp aspartic acid
E Glu glutamic acid
F Phe phenylalanine
G Gly glycine
H His histidine
I Ile isoleucine
K Lys lysine
L Leu leucine
M Met methionine
N Asn asparagine
P Pro proline
Q Gln glutamine
R Arg arginine
S Ser serine
T Thr threonine
V Val valine
W Trp tryptophan
Y Tyr tyrosine

We claim:

1. A monoclonal antibody or a monoclonal antibody derivative which specifically binds a peptide of SEQ ID NO:3, said monoclonal antibody derivative being selected from the group consisting of a monoclonal antibody conjugated to a cytotoxic agent or a radioisotope, and Fab, Fab' or F(ab')$_2$ fragments of said monoclonal antibody conjugated to a cytotoxic agent or radioisotope.

2. A hybridoma cell line producing the monoclonal antibody of claim 1.

3. A monoclonal antibody or a monoclonal antibody derivative which specifically binds a peptide of amino acid residues 1 to 420 of SEQ ID NO:7, said monoclonal antibody derivative being selected from the group consisting of a monoclonal antibody conjugated to a cytotoxic agent or a radioisotope, and Fab, Fab' or F(ab')$_2$ fragments of said monoclonal antibody conjugated to a cytotoxic agent or radioisotope.

4. A hybridoma cell line producing the monoclonal antibody of claim 3.

5. A monoclonal antibody or a monoclonal antibody derivative which specifically binds a peptide of amino acid residues 1 to 335 of SEQ ID NO:7, said monoclonal antibody derivative being selected from the group consisting of a monoclonal antibody conjugated to a cytotoxic agent or a radioisotope, and Fab, Fab' or F(ab')$_2$ fragments of said monoclonal antibody conjugated to a cytotoxic agent or radioisotope.

6. A hybridoma cell line producing the monoclonal antibody of claim 5.

* * * * *